US012661350B2

(12) United States Patent
Wertz et al.

(10) Patent No.: US 12,661,350 B2
(45) **Date of Patent: *Jun. 23, 2026**

(54) AMORPHOUS CABOZANTINIB PARTICLES AND USES THEREOF

(71) Applicant: FLEX PHARMA, LLC, Minneapolis, MN (US)

(72) Inventors: Christian F. Wertz, Saint Louis Park, MN (US); Tzehaw Chen, Corcoran, MN (US); Joseph McTarsney, Shakopee, MN (US)

(73) Assignee: Flex Pharma, LLC, New Brighton, MN (US)

( * ) Notice: Subject to any disclaimer, the term of this patent is extended or adjusted under 35 U.S.C. 154(b) by 396 days.

This patent is subject to a terminal disclaimer.

(21) Appl. No.: 18/201,975

(22) Filed: May 25, 2023

(65) Prior Publication Data

US 2023/0372325 A1 Nov. 23, 2023

Related U.S. Application Data

(63) Continuation of application No. PCT/US2021/060590, filed on Nov. 23, 2021.

(60) Provisional application No. 63/118,075, filed on Nov. 25, 2020.

(51) Int. Cl.
*A61K 31/47* (2006.01)
*A61K 9/14* (2006.01)

(52) U.S. Cl.
CPC .............. *A61K 31/47* (2013.01); *A61K 9/146* (2013.01)

(58) Field of Classification Search
CPC ................................ A61K 31/47; A61K 9/146
See application file for complete search history.

(56) References Cited

U.S. PATENT DOCUMENTS

| | | | |
|---|---|---|---|
| 6,093,557 | A | 7/2000 | Pui et al. |
| 6,350,786 | B1 | 2/2002 | Albano et al. |
| 6,399,362 | B1 | 6/2002 | Pui et al. |
| 6,746,869 | B2 | 6/2004 | Pui et al. |
| 6,764,720 | B2 | 7/2004 | Pui et al. |
| 7,247,338 | B2 | 7/2007 | Pui et al. |
| 7,279,322 | B2 | 10/2007 | Pui et al. |
| 7,498,063 | B2 | 3/2009 | Pui et al. |
| 7,579,473 | B2 | 8/2009 | Bannen et al. |
| 7,951,428 | B2 | 5/2011 | Hoerr et al. |
| 8,028,646 | B2 | 10/2011 | Pui et al. |
| 8,497,284 | B2 | 7/2013 | Bannen et al. |
| 8,585,942 | B2 | 11/2013 | Demirbüker |
| 8,585,943 | B2 | 11/2013 | Demirbüker |
| 8,841,303 | B2 | 9/2014 | Breitenbach et al. |
| 8,877,776 | B2 | 11/2014 | Brown et al. |
| 8,883,209 | B2 | 11/2014 | Babcock et al. |
| 8,974,827 | B2 | 3/2015 | Bloom et al. |
| 8,992,471 | B2 | 3/2015 | Dugas et al. |
| 8,992,603 | B2 | 3/2015 | Dugas et al. |
| 9,040,816 | B2 | 5/2015 | Gupta |
| 9,050,611 | B2 | 6/2015 | Pui et al. |
| 9,108,217 | B2 | 8/2015 | Hoerr et al. |
| 9,174,947 | B2 | 11/2015 | Bannen et al. |
| 9,211,261 | B2 | 12/2015 | Appel et al. |
| 9,248,217 | B2 | 2/2016 | Hoerr et al. |
| 9,456,992 | B2 | 10/2016 | Brisander et al. |
| 9,642,694 | B2 | 5/2017 | Hoerr et al. |
| 9,717,720 | B2 | 8/2017 | Wilson et al. |
| 9,724,342 | B2 | 8/2017 | Wilson et al. |
| 9,809,549 | B2 | 11/2017 | Brown et al. |
| 9,815,789 | B2 | 11/2017 | Jetti et al. |
| 9,827,230 | B2 | 11/2017 | Brisander et al. |
| 9,833,442 | B2 | 12/2017 | Brisander et al. |
| 9,833,443 | B2 | 12/2017 | Brisander et al. |
| 9,861,624 | B2 | 1/2018 | Aftab |
| 9,969,692 | B2 | 5/2018 | Wilson et al. |
| 10,034,873 | B2 | 7/2018 | Wilson et al. |
| 10,039,757 | B2 | 8/2018 | Wilson et al. |
| 10,053,427 | B2 | 8/2018 | Stefinovic et al. |
| 10,123,999 | B2 | 11/2018 | Wilson |
| 10,143,683 | B2 | 12/2018 | Brisander et al. |
| 10,159,666 | B2 | 12/2018 | Aftab et al. |
| 10,166,225 | B2 | 1/2019 | Aftab et al. |
| 10,206,916 | B2 | 2/2019 | Stefinovic et al. |
| 10,252,289 | B2 | 4/2019 | Hoerr et al. |
| 10,314,829 | B2 | 6/2019 | Brisander et al. |
| 10,314,830 | B2 | 6/2019 | Brisander et al. |
| 10,501,418 | B2 | 12/2019 | Aftab et al. |
| 10,543,206 | B2 | 1/2020 | Wilson et al. |

(Continued)

FOREIGN PATENT DOCUMENTS

| | | |
|---|---|---|
| EP | 1920767 A1 | 9/2006 |
| EP | 0988863 B2 | 3/2009 |

(Continued)

OTHER PUBLICATIONS

Tanno et al. (Drug Development and Industrial Pharmacy, 2004, vol. 30, No. 1, p. 9-17) (Year: 2004).*
Ali et al., "Tackling the challenges with poorly soluble drugs," Sep. 2, 2015, *J Anal Pharm Res*, 1(1):1-3.
Bikiaris, "Solid dispersions, Part I: recent evolutions and future opportunities in manufacturing methods for dissolution rate enhancement of poorly water-soluble drugs," Sep. 16, 2011, *Expert Opin Drug Deliv*, 8(11): 1501-1519.
Bikiaris, "Solid dispersions, part II: new strategies in manufacturing methods for dissolution rate enhancement of poorly water-soluble drugs," Sep. 16, 2011, *Expert Opin Drug Deliv*, 8(12):1663-1680.
Chaudhari et al., "Evaluating the effects of different molecular weights of polymers in stabilizing supersaturated drug solutions and formulations using various methodologies of the model drug: Fenofibrate," Sep. 2015, *J Pharm Sci and Pharmacol*, 2(3): 259-276.

(Continued)

*Primary Examiner* — James D. Anderson
(74) *Attorney, Agent, or Firm* — Mueting Raasch Group

(57) ABSTRACT

Amorphous solid dispersions of the protein kinase inhibitor cabozantinib. The amorphous solid dispersions exhibit chemical and physical stability under stressed conditions. The amorphous solid dispersions may be suitable for use in pharmaceutical compositions for administration to human subjects or patients.

28 Claims, No Drawings

(56) References Cited

U.S. PATENT DOCUMENTS

| | | | |
|---|---|---|---|
| 10,548,888 | B2 | 2/2020 | Wilson et al. |
| 10,555,937 | B2 | 2/2020 | Brisander et al. |
| 10,561,643 | B2 | 2/2020 | Brisander et al. |
| 10,561,644 | B2 | 2/2020 | Brisander et al. |
| 10,561,645 | B2 | 2/2020 | Brisander et al. |
| 10,772,877 | B2 | 9/2020 | Brisander et al. |
| 10,874,671 | B2 | 12/2020 | Jain et al. |
| 11,091,439 | B2 | 8/2021 | Brown et al. |
| 11,091,440 | B2 | 8/2021 | Brown et al. |
| 11,098,015 | B2 | 8/2021 | Brown et al. |
| 11,141,413 | B2 | 10/2021 | Aftab et al. |
| 11,241,419 | B2 | 2/2022 | Brisander et al. |
| 11,279,675 | B2 | 3/2022 | Shah |
| 11,298,349 | B2 | 4/2022 | Wilson et al. |
| 11,376,243 | B2 | 7/2022 | Brisander et al. |
| 2008/0063708 | A1 | 3/2008 | Perlman et al. |
| 2009/0203709 | A1 | 8/2009 | Steinberg et al. |
| 2010/0143459 | A1 | 6/2010 | Liepold et al. |
| 2010/0240672 | A1 | 9/2010 | Breitenbach et al. |
| 2010/0266692 | A1 | 10/2010 | Bloom et al. |
| 2010/0308483 | A1 | 12/2010 | Demirbüker |
| 2010/0308484 | A1 | 12/2010 | Demirbüker |
| 2011/0229627 | A1 | 9/2011 | Hoerr et al. |
| 2011/0306632 | A1 | 12/2011 | Miller et al. |
| 2012/0264833 | A1 | 10/2012 | Babcock et al. |
| 2012/0295988 | A1 | 11/2012 | Babcock et al. |
| 2013/0323403 | A1 | 12/2013 | Hoerr et al. |
| 2014/0158787 | A1 | 6/2014 | Chen et al. |
| 2014/0356443 | A1 | 12/2014 | Brisander et al. |
| 2014/0378454 | A1 | 12/2014 | Brisander et al. |
| 2015/0190253 | A1 | 7/2015 | Dugas et al. |
| 2016/0022662 | A1 | 1/2016 | DeCillis |
| 2016/0082019 | A1 | 3/2016 | Sweeney et al. |
| 2016/0175881 | A1 | 6/2016 | Lasch et al. |
| 2016/0235677 | A1 | 8/2016 | Hoerr et al. |
| 2016/0250153 | A1 | 9/2016 | Brisander et al. |
| 2016/0361313 | A1 | 12/2016 | Brisander et al. |
| 2017/0087143 | A1 | 3/2017 | Aftab et al. |
| 2017/0096395 | A1 | 4/2017 | Jetti et al. |
| 2017/0143683 | A1 | 5/2017 | Brisander et al. |
| 2017/0143715 | A1 | 5/2017 | Brisander et al. |
| 2017/0209372 | A1 | 7/2017 | Temtem et al. |
| 2018/0042906 | A1 | 2/2018 | Brisander et al. |
| 2018/0104618 | A1 | 4/2018 | Fonseca et al. |
| 2018/0110769 | A1 | 4/2018 | Stefinovic et al. |
| 2018/0111903 | A1 | 4/2018 | Stefinovic et al. |
| 2019/0060294 | A1 | 2/2019 | Brisander et al. |
| 2019/0076413 | A1 | 3/2019 | Brisander et al. |
| 2019/0193109 | A1 | 6/2019 | Hoerr et al. |
| 2019/0255029 | A1 | 8/2019 | Brisander et al. |
| 2019/0275018 | A1 | 9/2019 | Brisander et al. |
| 2019/0275019 | A1 | 9/2019 | Brisander et al. |
| 2019/0282553 | A1 | 9/2019 | Brisander et al. |
| 2020/0113903 | A1 | 4/2020 | Liu et al. |
| 2020/0170934 | A1 | 6/2020 | Beier et al. |
| 2020/0190032 | A1 | 6/2020 | Brown et al. |
| 2020/0253941 | A1 | 8/2020 | Brisander et al. |
| 2020/0261426 | A1 | 8/2020 | Park et al. |
| 2020/0261449 | A1 | 8/2020 | Jain et al. |
| 2021/0093616 | A1 | 4/2021 | Brisander et al. |
| 2022/0117947 | A1 | 4/2022 | Brisander et al. |
| 2022/0160687 | A1 | 5/2022 | Brisander et al. |
| 2022/0265633 | A1 | 8/2022 | Dube et al. |
| 2022/0280500 | A1 | 9/2022 | Dube et al. |
| 2022/0362235 | A1 | 11/2022 | Dube et al. |
| 2022/0387418 | A1 | 12/2022 | Dube et al. |
| 2023/0041852 | A1 | 2/2023 | Wertz et al. |
| 2023/0142737 | A1 | 5/2023 | Liu et al. |

FOREIGN PATENT DOCUMENTS

| | | | |
|---|---|---|---|
| EP | 3705118 | A1 | 9/2020 |
| WO | WO 2005/030140 | A2 | 4/2005 |
| WO | WO 2007/089881 | A2 | 8/2007 |
| WO | WO 2007/089883 | A2 | 8/2007 |
| WO | WO 2008/055965 | A1 | 5/2008 |
| WO | WO 2008/055966 | A1 | 5/2008 |
| WO | WO 2008/094700 | A3 | 8/2008 |
| WO | WO 2009/010837 | A2 | 1/2009 |
| WO | WO 2009/061787 | A1 | 5/2009 |
| WO | WO 2009/072950 | A1 | 6/2009 |
| WO | WO 2009/072953 | A1 | 6/2009 |
| WO | WO 2009/100176 | A2 | 8/2009 |
| WO | WO 2010/083414 | A1 | 7/2010 |
| WO | WO 2012/009722 | A1 | 1/2012 |
| WO | WO 2012/099961 | A2 | 7/2012 |
| WO | WO 2013/105894 | A1 | 7/2013 |
| WO | WO 2013/105895 | A1 | 7/2013 |
| WO | WO 2014/003677 | A1 | 1/2014 |
| WO | WO 2014/003678 | A1 | 1/2014 |
| WO | WO 2015/123639 | A1 | 8/2015 |
| WO | WO 2015/177758 | A1 | 11/2015 |
| WO | WO 2016/016665 | A1 | 2/2016 |
| WO | WO 2016/019285 | A1 | 2/2016 |
| WO | WO 2016/086193 | A1 | 6/2016 |
| WO | WO 2016/105982 | A1 | 6/2016 |
| WO | WO 2016/150963 | A1 | 9/2016 |
| WO | WO 2018/064191 | A1 | 4/2018 |
| WO | WO 2018/104954 | A1 | 6/2018 |
| WO | WO 2018/218233 | A1 | 11/2018 |
| WO | WO 2019/241504 | A1 | 12/2019 |
| WO | WO 2020/115140 | A1 | 6/2020 |
| WO | WO 2020/172120 | A1 | 8/2020 |
| WO | WO 2020/229702 | A1 | 11/2020 |
| WO | WO 2021/138483 | A1 | 7/2021 |
| WO | WO 2021/150981 | A1 | 7/2021 |
| WO | WO 2021/152129 | A1 | 8/2021 |
| WO | WO 2021/155254 | A1 | 8/2021 |
| WO | WO 2021/222739 | A1 | 11/2021 |
| WO | WO 2021/239709 | A1 | 12/2021 |
| WO | WO 2021/239744 | A1 | 12/2021 |
| WO | WO 2022/040446 | A1 | 2/2022 |
| WO | WO 2022/106985 | A1 | 5/2022 |
| WO | WO 2022/115464 | A1 | 6/2022 |
| WO | WO 2022/177983 | A1 | 8/2022 |

OTHER PUBLICATIONS

Gala et al., "Harnessing the therapeutic potential of anticancer drugs through amorphous solid dispersions," Jan. 1, 2020, *BBA—Reviews on Cancer*, 1873(1), 188319.

Gurunath et al., "Amorphous solid dispersion method for improving oral bioavailability of poorly water-soluble drugs," Apr. 5, 2013, *J Pharm Res*, 6(4):476-480.

Herbrink et al., "Inherent formulation issues of kinase inhibitors," Oct. 10, 2016, *J Control Release*, 236:118-127.

Herbrink, "Pharmaceutics of oral anticancer agents and stimulants," PhD Thesis, Netherlands Cancer Institute, Jun. 2018, 316 pages.

Hoshino-Yoshino et al., "Bridging from preclinical to clinical studies for Tyrosine Kinase inhibitors based on pharmacokinetics/pharmacodynamics and toxicokinetics/toxicodyamics," Sep. 6, 2011, *Drug Metabolism and Pharmacokinetics*, 26(6):612-620.

Huang et al., "Fundamental aspects of solid dispersion technology for poorly soluble drugs," Feb. 1, 2014, *Acta Pharmaceutica Sinica B*, 4(1):18-25.

Jesson et al., "Carbon dioxide-mediated generation of hybrid nanoparticles for improved bioavailability of protein kinase inhibitors," Mar. 2014, *Pharm Res*, 31:694-705.

Karagianni et al., "Co-Amorphous solid dispersions for solubility and absorption improvement of drugs: Composition, Preparation, Characterization and Formulations for Oral Delivery," Jul. 19, 2018, *Pharmaceutics*, 10(3):98-123.

Leuner et al., "Improving drug solubility for oral delivery using solid dispersions," Feb. 7, 2000, *Eur J Pharm Biopharm*, 50(1):47-60.

Nguyen et al., "Pharmaceutical applications of electrospraying," Jun. 7, 2016, *J Pharm Sci*, 105(9):2601-2620.

Nikghalb et al., "Solid dispersion: methods and polymers to increase the solubility of poorly soluble drugs," Oct. 30, 2012, *J Appl Pharm Sci*, 2(10):170-175.

(56) References Cited

OTHER PUBLICATIONS

Sawicki et al., "Inventory of oral anticancer agents: pharmaceutical formulation aspects with focus on the solid dispersion technique," Oct. 21, 2016, *Cancer Treat Rev*, 50:247-263.
Sridhar et al., "Electrosprayed nanoparticles for drug delivery and pharmaceutical applications," Jul. 19, 2013, *Biomatter*, 3(3):e24281.
Tron et al., "Overview of the manufacturing methods of solid dispersion technology for improving the solubility of poorly water-soluble drugs and application to anticancer drugs," Mar. 19, 2019, *Pharmaceutics*, 11(3):132.
Williams et al., "Enhancing the oral absorption of kinase inhibitors using lipophilic salts and lipid-based formulations," Oct. 30, 2018, *Mol Pharmaceutics*, 15(12):5678-5696.
Zhang et al., "Processing impact on performance of solid dispersions," Aug. 30, 2018, *Pharmaceutics*, 10(3):142.

* cited by examiner

AMORPHOUS CABOZANTINIB PARTICLES AND USES THEREOF

REFERENCE TO RELATED APPLICATION

The present application is a continuation of International Application No. PCT/US2021/060590, filed Nov. 23, 2021, which claims the benefit of U.S. Provisional App. No. 63/118,075 (filed Nov. 25, 2020), the entire disclosures of which are hereby incorporated by reference.

BACKGROUND

Protein kinase inhibitors (PKIs) have been studied for their potential use in treating various disorders of cellular proliferation, including cancer. The potential for PKIs as a treatment is based on the role that protein kinases are known to play in regulating many cellular pathways, including those involved in signal transduction. Dysregulation of protein kinases has been implicated in the development and progression of many cancers, which suggests that PKIs may be useful as a treatment for disorders or diseases such as cancer that are caused by uncontrolled overexpression or upregulation of protein kinases.

One such PKI is cabozantinib. In vitro biochemical and/or cellular assays have shown that cabozantinib inhibits the tyrosine kinase activity of MET, VEGFR-1, -2 and -3, AXL, RET, ROS1, TYRO3, MER, KIT, TRKB, FLT-3, and TIE-2. These receptor tyrosine kinases are involved in both normal cellular function and pathologic processes such as oncogenesis, metastasis, tumor angiogenesis, drug resistance, and maintenance of the tumor microenvironment.

Cabozantinib (in the (S)-malate salt form) is currently marketed as an immediate-release tablet formulation for oral administration under the brand name CABOMETYX. CABOMETYX is indicated for (a) treatment of patients with advanced renal cell carcinoma (RCC), (b) treatment of patients with hepatocellular carcinoma (HCC) who have been previously treated with sorafenib, and (c) certain patients with locally advanced or metastatic differentiated thyroid cancer (DTC). The recommended dose for CABOMETYX is 60 mg once per day, or 40 mg once per day for certain pediatric patients and certain combination therapies.

Cabozantinib (S)-malate is also currently marketed as an immediate-release capsule formulation for oral administration under the brand name COMETRIQ. COMETRIQ is indicated for the treatment of patients with progressive, metastatic medullary thyroid cancer (MTC). The recommended daily dose of COMETRIQ is 140 mg once per day.

The two formulations exhibit similar bioavailability. Per the labeling information for CABOMETYX, a 19% increase in maximum plasma concentration ($C_{max}$) was observed for the tablet formulation as compared to the capsule formulation (COMETRIQ) following administration of a single 140 mg dose. A less than 10% difference in AUC was observed in exposure (expressed as area-under-the-curve, or "AUC").

Cabozantinib accumulates in the body and has a long elimination half-life. Repeat daily dosing (140 mg/day) of COMETRIQ for 19 days resulted in 4- to 5-fold mean cabozantinib accumulation (based on AUC) compared to a single dose administration; steady state was achieved by Day 15. For COMETRIQ the predicted effective half-life is approximately 55 hours. For CABOMETYX the predicted terminal half-life is approximately 99 hours. Cabozantinib is highly protein bound in human plasma (≥99.7%).

Oral dosage of these formulations is accompanied by a food effect. An increase in exposure and/or maximum plasma concentration is known to occur when CABOMETYX or COMETRIQ is taken with food. Per the labeling information for COMETRIQ, administration of a single 140-mg dose of COMETRIQ to healthy subjects with a high-fat meal resulted in a 41% increase in $C_{max}$ and a 57% increase in AUC.

Because of the observed food effect, the prescribing information for CABOMETYX specifically states "Do not administer CABOMETYX with food." The prescribing information instructs that CABOMETYX should be administered at least 1 hour before or at least two hours after eating. Similarly, the prescribing information for COMETRIQ states that COMETRIQ should be administered "without food" and that patients should be instructed "not to eat for at least 2 hours before and at least 1 hour after taking COMETRIQ."

Excess exposure to any drug can lead to undesirable side effects. The prescribing information for COMETRIQ references a known incident of overdosage, which was reported to result in Grade 3 memory impairment, Grade 3 mental status changes, Grade 3 cognitive disturbance, Grade 2 weight loss, and Grade 1 increase in BUN (blood urea nitrogen) for the affected patient.

Increased serum levels may also exacerbate or increase the prevalence of more common side effects such as diarrhea, stomatitis, palmar-plantar erythrodysesthesia (PPE), decreased weight, decreased appetite, nausea, fatigue, oral pain, hair color changes, dysgeusia, hypertension, abdominal pain, constipation, and the like.

The requirement to take CABOMETYX or COMETRIQ without food (for a three-hour period for each dose) is a considerable burden to patients. In addition, administration of CABOMETYX or COMETRIQ is commonly (10-30% of patients or more) accompanied by gastrointestinal side effects such as diarrhea, stomatitis, nausea, constipation, abdominal pain, vomiting, dysphagia, dyspepsia, and decreased appetite. These side effects may be worsened or more prevalent because of the restrictions on food intake.

Poor adherence to the dosing recommendations can be very detrimental to patients. A patient may forgo taking regular doses of CABOMETYX or COMETRIQ due to the food effect and/or dosing restrictions, and poor compliance could result, with the patient being deprived the benefit of therapy.

Thus, there remains a need in the art for a means for a wide variety of patients to receive the full benefits of cabozantinib therapy, while minimizing the risk of experiencing adverse side effects, especially those that are associated with the food effect observed for CABOMETYX and COMETRIQ. In short, there is a need in the art for an effective cabozantinib therapy that is largely insensitive to the fasted/fed status of the patient.

SUMMARY OF DISCLOSURE

The present disclosure relates to the field of amorphous solid dispersions and pharmaceutical compositions of the protein kinase inhibitor cabozantinib. The present disclosure also relates to methods of treatment involving the administration of amorphous solid dispersions and pharmaceutical compositions of cabozantinib.

An aspect of the disclosure relates to an amorphous solid dispersion ("ASD") of cabozantinib. The ASD comprises cabozantinib and one or more polymers. In another aspect, the present disclosure provides a pharmaceutical composition comprising the ASD.

Yet another aspect of the disclosure relates to methods of treating a disease which responds to an inhibition of protein kinase activity, such as a proliferative disorder. The methods comprise administering an ASD or a pharmaceutical composition of the present disclosure to a patient.

DETAILED DESCRIPTION

The present disclosure relates to the field of amorphous solid dispersions and pharmaceutical compositions of the protein kinase inhibitor cabozantinib. The ASDs and pharmaceutical compositions of the present disclosure may provide particular advantages over immediate-release cabozantinib formulations, such as CABOMETYX and COMETRIQ. For example, certain pharmaceutical compositions of the present disclosure may provide an enhanced bioavailability and/or enhanced pharmacokinetic performance. Based on improved bioavailability or enhanced pharmacokinetics, a reduced dosage may be possible, for example. Thus, the ASDs and pharmaceutical compositions of the present disclosure may offer a safer but equally effective presentation of cabozantinib as compared to the currently available commercial products.

Cabozantinib

Cabozantinib is a kinase inhibitor with the chemical name N-(4-(6,7-dimethoxyquinolin-4-yloxy)phenyl)-N'-(4-fluorophenyl)cyclopropane-1,1-dicarboxamide, (2S)-hydroxybutanedioate. Cabozantinib is disclosed in U.S. Pat. No. 7,579,473 to Bannen, et al. and crystalline forms are disclosed in U.S. Pat. No. 10,501,418 to Aftab, et al. Cabozantinib has a molecular weight of 501.5 g/mol.

The active ingredient in CABOMETYX and COMETRIQ is the (S)-malate salt of cabozantinib having the following structure:

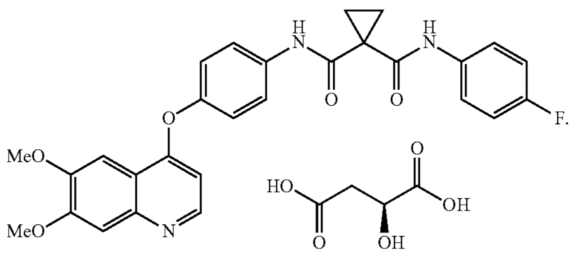 [SMILES: COc1cc2nccc(Oc3ccc(NC(=O)C4(C(=O)Nc5ccc(F)cc5)CC4)cc3)c2cc1OC ; O=C(O)C[C@H](O)C(=O)O]

Malate salts of cabozantinib are disclosed in U.S. Pat. No. 8,877,776 to Brown, et al. and U.S. Pat. No. 9,809,549 to Brown, et al. The molecular formula for cabozantinib (S)-malate is $C_{28}H_{24}FN_3O_5 \cdot C_4H_6O_5$, which corresponds to a molecular weight of 635.6 g/mol. Cabozantinib (S)-malate salt is a white to off-white solid that is practically insoluble in aqueous media.

Cabozantinib (S)-malate is currently marketed as an immediate-release tablet formulation for oral administration under the brand name CABOMETYX. Currently available CABOMETYX tablets are labeled as containing 20 mg cabozantinib base (equivalent to 25 mg cabozantinib (S)-malate), 40 mg cabozantinib base (equivalent to 51 mg cabozantinib (S)-malate), or 60 mg cabozantinib base (equivalent to 76 mg cabozantinib (S)-malate). CABOMETYX tablets include the following inactive ingredients: microcrystalline cellulose, lactose anhydrous, hydroxypropyl cellulose, croscarmellose sodium, colloidal silicon dioxide, and magnesium stearate.

Cabozantinib S-malate is also currently marketed as an immediate-release capsule formulation for oral administration under the brand name COMETRIQ. Currently available COMETRIQ capsules are labeled as containing 20 mg cabozantinib base (equivalent to 25 mg cabozantinib (S)-malate) or 80 mg cabozantinib base (equivalent to 102 mg cabozantinib (S)-malate). The fill material for COMETRIQ includes the following inactive ingredients: silicified microcrystalline cellulose, croscarmellose sodium, sodium starch glycolate, fumed silica, and stearic acid.

Amorphous Solid Dispersions of Cabozantinib

The pharmaceutical compositions of the present disclosure comprise ASDs of cabozantinib. The ASDs of the disclosure comprise cabozantinib and one or more polymers. A pharmaceutically suitable amorphous solid dispersion generally comprises a pharmaceutically active ingredient, such as cabozantinib, dispersed in a pharmacologically inert carrier, such as a polymer. One aim of a pharmaceutically suitable amorphous solid dispersion is to improve the bioavailability of the pharmaceutically active ingredient. This improvement can occur, for example, because of enhanced surface area, improved wettability or dispersibility, increased dissolution rate, or other factors.

In general, it is favorable if the pharmaceutically active ingredient is dispersed in the polymer to form what has been termed in the art as a "glass solution." However, other forms of dispersion, such as those termed as "solid solution" or "glass suspension," may also be suitable. The precise characterization of the solid dispersion is not important, provided that the amorphous solid dispersion is capable of providing desired characteristics and performance.

Cabozantinib.

In the ASDs of the disclosure, the cabozantinib may be as a free base, or as a salt such as a malate salt or other pharmaceutically acceptable salt. The cabozantinib may also be anhydrous, or a hydrate (such as monohydrate). In some embodiments, the cabozantinib is cabozantinib free base, anhydrous. In other embodiments, the cabozantinib is as an anhydrous malate salt. In yet other embodiments, the cabozantinib is as an anhydrous (S)-malate salt. In the description of the amorphous solid dispersions below, any reference to "cabozantinib" refers broadly to cabozantinib free base, salts of cabozantinib, anhydrous cabozantinib (or salts thereof), hydrates or solvates of cabozantinib, and hydrates or solvates of cabozantinib salts as suitable alternatives, unless specified.

Polymers.

The one or more polymers, which should be pharmaceutically acceptable polymers, may be suitable to provide structure and stability to the ASD. Polymers that can be used in the ASDs of the present disclosure may include, but are not limited to, those described below. The term "polymer" includes, but is not limited to, organic homopolymers, copolymers (such as for example, block, graft, random, and terpolymers, etc.), and blends and modifications thereof. The term "copolymer" refers to polymers containing two or more different monomeric units or segments, and includes terpolymers, tetrapolymers, etc. Information regarding suitable polymers, and commercial sources therefor, can be found in Sheskey P J (ed.) *Handbook of Pharmaceutical Excipients, 9th Ed.* London: Pharmaceutical Press; 2020 (ISBN 0857113755); alternatively, the most up-to-date edition of the same title may be consulted.

In certain embodiments, the ASD consists of cabozantinib and the one or more polymers. In certain other embodiments, the ASD consists essentially of cabozantinib and the one or more polymers. Polymers that can be used in the ASDs of the present disclosure may include, but are not limited to, those described below.

Polymers that can be used in the ASDs of the present disclosure may include ionizable or non-ionizable polymers, or a combination thereof.

In some embodiments, the one or more polymers may be non-ionizable polymers. In certain embodiments, the ASD consists of cabozantinib and one or more non-ionizable polymers. In certain other embodiments, the ASD consists essentially of cabozantinib and one or more non-ionizable polymers.

In some embodiments, the one or more polymers may be ionizable polymers. In certain embodiments, the ASD consists of cabozantinib and one or more ionizable polymers. In certain other embodiments, the ASD consists essentially of cabozantinib and one or more ionizable polymers.

In yet other embodiments, a combination of ionizable and non-ionizable polymers may be used. In certain embodiments, the ASD consists of cabozantinib and a combination of one or more non-ionizable polymers and one or more ionizable polymers. In certain other embodiments, the ASD consists essentially of cabozantinib and a combination of one or more non-ionizable polymers and one or more ionizable polymers.

Polymers that can be used in the ASDs of the present disclosure may include polymers that exhibit pH-dependent solubility, or polymers that are generally insensitive to pH, or a combination thereof.

In some embodiments, the one or more polymers may exhibit pH-dependent solubility. In certain embodiments, the ASD consists of cabozantinib and one or more polymers that exhibits pH-dependent solubility. In certain other embodiments, the ASD consists essentially of cabozantinib and one or more polymers that exhibits pH-dependent solubility.

In other embodiments, the one or more polymers may be generally insensitive to pH. In certain embodiments, the ASD consists of cabozantinib and one or more polymers generally insensitive to pH. In certain other embodiments, the ASD consists essentially of cabozantinib and one or more polymers generally insensitive to pH.

In yet other embodiments, a combination of polymers may include one or more polymers exhibiting pH-dependent solubility and one or more polymers generally insensitive to pH. In certain embodiments, the ASD consists of cabozantinib and a combination of one or more polymers exhibiting pH-dependent solubility and one or more polymers generally insensitive to pH. In certain other embodiments, the ASD consists essentially of cabozantinib and a combination of one or more polymers exhibiting pH-dependent solubility and one or more polymers generally insensitive to pH.

Non-Ionizable Polymers.

Suitable non-ionizable polymers may include: polysaccharides and polysaccharide derivatives (including cellulose ethers and non-ionizable cellulose esters); polymers or copolymers of N-vinylpyrrolidone and/or vinyl acetate; polymers of ethylene oxide; homopolymers or copolymers of lactic acid and/or glycolic acid; maleic anhydride copolymers; polyvinyl caprolactam-polyvinyl acetate-polyethylene glycol graft copolymer; and poloxamers.

Suitable non-ionizable polysaccharides and polysaccharide derivatives may include cellulose ethers and non-ionizable cellulose esters. Examples of suitable cellulose ethers include methylcellulose ("MC"; e.g., METHOCEL A15 LV, METHOCEL A4M), ethylcellulose ("EC"; e.g., ETHOCEL), hypromellose or hydroxypropyl methylcellulose ("HPMC"; e.g., METHOCEL E3, METHOCEL E5, METHOCEL E6, METHOCEL E15, AFFINISOL HPMC HME), hydroxyethyl cellulose ("HEC"; e.g., NATROSOL 250 Pharm), and hydroxypropyl cellulose ("HPC"; e.g., HPC EF, HPC LF, HPC JF, HPC L, KLUCEL).

Examples of non-ionizable cellulose esters that may be suitable include cellulose acetate, cellulose propionate, cellulose butyrate, and cellulose acetate butyrate.

Examples of suitable polymers or copolymers of N-vinylpyrrolidone and/or vinyl acetate include polyvinylpyrrolidone ("PVP"; e.g., PVP K25, PVP K90, VIVAPHARM PVP), crospovidone or crosslinked polyvinylpyrrolidone (e.g., KOLLIDON CL, VIVAPHARM PVPP), copovidone or vinylpyrrolidone/vinyl acetate copolymer ("PVP/VA"; e.g., KOLLIDON VA 64, VIVAPHARM PVP/VA 64), and polyvinyl alcohol ("PVA"; e.g., VIVAPHARM PVA).

Examples of suitable polymers of ethylene oxide include polyethylene glycol ("PEG"; e.g., KOLLISOLV PEG 8000) and poly(ethylene oxide) ("PEO"; e.g., POLYOX).

Examples of suitable homopolymers or copolymers of lactic acid and/or glycolic acid include polylactide or poly (lactic acid) ("PLA"), polyglycolide or poly(glycolic acid) ("PGA"), and poly(lactic-co-glycolic acid) ("PLGA").

Non-ionizable maleic anhydride copolymers such as poly (methyl vinyl ether/maleic anhydride) ("PVM/MA") may also be suitable. Non-ionizable poloxamers (e.g., PLURONIC, KOLLIPHOR) may also be suitable.

A polyvinyl caprolactam-polyvinyl acetate-polyethylene glycol graft copolymer (e.g., SOLUPLUS) may also be a suitable non-ionizable polymer.

Ionizable Polymers.

Suitable ionizable polymers may be considered "anionic" or "cationic" polymers. Anionic and cationic polymers often exhibit pH-dependent solubility.

Anionic polymers often include carboxylate (such as acetate), phthalate, succinate or acrylate functionalities. Anionic polymers are generally insoluble at low pH and more soluble at higher pH. Suitable anionic polymers may include anionic polysaccharides and polysaccharide derivatives (such as ionizable cellulose esters), copolymers of methacrylic acid and/or alkyl acrylate, and derivatized vinyl acetate polymers, for example.

An example of an ionizable polysaccharide that may be suitable is xanthan gum. Examples of suitable ionizable cellulose esters may include carboxymethylcellulose ("CMC"; carboxymethylcellulose sodium), hypromellose acetate succinate, or hydroxypropyl methylcellulose acetate succinate ("HPMC-AS"; e.g., AFFINISOL HPMC-AS, AQUASOLVE, AQOAT), hydroxypropyl methylcellulose phthalate ("HPMC-P"; e.g., HP-50, HP-55), and cellulose acetate phthalate ("CAP"; e.g., Eastman C-A-P).

Suitable copolymers of methacrylic acid and/or alkyl methacrylate may include methacrylic acid/methyl methacrylate copolymer (e.g., EUDRAGIT L100) and methacrylic acid/ethyl acrylate copolymer (e.g., EUDRAGIT L100-55, KOLLICOAT MAE).

An example of a derivatized vinyl acetate polymer that may be suitable is polyvinyl acetate phthalate ("PVA-P"; e.g., PHTHALAZIN).

Cationic polymers often include amine functionalities. Cationic polymers are generally soluble at low pH and less soluble at higher pH. Suitable cationic polymers may include cationic polysaccharides and polysaccharide derivatives, and amine-functionalized copolymers of methacrylic acid and/or alkyl acrylate, for example.

An example of a cationic polysaccharide that may be suitable is chitosan.

Suitable amine-functionalized copolymers of methacrylic acid and/or alkyl acrylate include, for example, dimethylaminoethyl methacrylate/butyl methacrylate/methyl methacrylate copolymer (e.g., EUDRAGIT E100) and aminoalkyl methacrylate copolymer such as poly(ethyl acrylate-co-methyl methacrylate-co-trimethylammonioethyl methacrylate chloride (e.g., EUDRAGIT RL100, EUDRAGIT RL PO, EUDRAGIT RS PO).

Amorphous Solid Dispersions.

The pharmaceutical compositions of the present disclosure comprise amorphous solid dispersions of cabozantinib, which comprise cabozantinib and one or more polymers. In some embodiments, the one or more polymers includes one or more polymers from those identified above.

In other embodiments, the one or more polymers includes one or more polymers from those identified above, with the proviso that a polymer of polyethylene oxide is not present in the ASD. In yet other embodiments, the one or more polymers includes one or more polymers from those identified above, with the proviso that the ASD is substantially free from polymers of polyethylene oxide.

In other embodiments, the one or more polymers includes one or more polymers from those identified above, with the proviso that polyethylene glycol is not present in the ASD. In yet other embodiments, the one or more polymers includes one or more polymers from those identified above, with the proviso that the ASD is substantially free from polyethylene glycol.

In still other embodiments, the one or more polymers includes one or more polymers from those identified above, with the proviso that a cationic polymer is not present in the ASD. In yet other embodiments, the one or more polymers includes one or more polymers from those identified above, with the proviso that the ASD is substantially free from cationic polymers.

In still other embodiments, the one or more polymers includes one or more polymers from those identified above, with the proviso that dimethylaminoethyl methacrylate/butyl methacrylate/methyl methacrylate copolymer (e.g., EUDRAGIT E100) is not present in the ASD. In yet other embodiments, the one or more polymers includes one or more polymers from those identified above, with the proviso that the ASD is substantially free from dimethylaminoethyl methacrylate/butyl methacrylate/methyl methacrylate copolymer (e.g., EUDRAGIT E100).

In some embodiments, the one or more polymers includes one or more polymers from those identified above, with the proviso that polyvinyl caprolactam-polyvinyl acetate-polyethylene glycol graft copolymer (e.g., SOLUPLUS) is not present in the ASD. In yet other embodiments, the one or more polymers includes one or more polymers from those identified above, with the proviso that the ASD is substantially free from polyvinyl caprolactam-polyvinyl acetate-polyethylene glycol graft copolymer (e.g., SOLUPLUS).

In certain embodiments, the ASD comprises cabozantinib and one or more non-ionizable polymers. In certain embodiments, the ASD consists of cabozantinib and one or more non-ionizable polymers. In certain other embodiments, the ASD consists essentially of cabozantinib and one or more non-ionizable polymers.

In certain embodiments, the ASD comprises cabozantinib and one or more non-ionizable cellulose ethers. In certain embodiments, the ASD consists of cabozantinib and one or more non-ionizable cellulose ethers. In certain other embodiments, the ASD consists essentially of cabozantinib and one or more non-ionizable cellulose ethers. In any of the foregoing, the non-ionizable cellulose ether can be methylcellulose, ethylcellulose, hydroxypropyl methylcellulose, hydroxyethyl cellulose, or hydroxypropyl cellulose, for example. In certain embodiments, hydroxypropyl methylcellulose or hydroxypropyl cellulose may be particularly suitable.

In some embodiments, the one or more polymers comprises a hydroxypropyl methylcellulose (also known as "hypromellose" or "HPMC"), such as METHOCEL E3, METHOCEL E5, METHOCEL E6, or METHOCEL E15, for example. These METHOCEL grades are non-ionic water-soluble cellulose ethers, characterized by a methoxyl substitution of 28 to 30%, and a hydroxypropoxyl substitution of 7 to 12%. These grades are characterized by a low solution viscosity (as determined at 20° C. for a 2% solution in water, according to manufacturer's specifications), where the grade number indicates the midpoint of the viscosity range (e.g., METHOCEL E3 is characterized a viscosity of 2.4-3.6 mPa·s; METHOCEL E5 is characterized a viscosity of 4.0-6.0 mPa·s). These grades are considered low molecular-weight HPMC products, having a number average molecular weight (Mn) of about 20 kDa or lower.

In some embodiments, the one or more polymers comprise a hydroxypropyl methylcellulose (such as METHOCEL E3, METHOCEL E5, METHOCEL E6, or METHOCEL E15, for example). In certain embodiments, the one or more polymers consists of a hydroxypropyl methylcellulose. In certain embodiments, the one or more polymers consists essentially of a hydroxypropyl methylcellulose. While all these grades are suitable for use in the ASDs of the disclosure, METHOCEL E5 has been demonstrated to be particularly suitable. A combination or mixture of grades of hydroxypropyl methylcellulose may also be employed.

In some embodiments, the one or more polymers comprise a low molecular-weight hydroxypropyl methylcellulose. In certain embodiments, the one or more polymers consists of a low molecular-weight hydroxypropyl methylcellulose. In certain embodiments, the one or more polymers consists essentially of a low molecular-weight hydroxypropyl methylcellulose.

In some embodiments, the one or more polymers comprise a low molecular-weight hydroxypropyl methylcellulose characterized by a solution viscosity of 4.0-6.0 mPa·s. In certain embodiments, the one or more polymers consists of a low molecular-weight hydroxypropyl methylcellulose characterized by a solution viscosity of 4.0-6.0 mPa·s. In certain embodiments, the one or more polymers consists essentially of a low molecular-weight hydroxypropyl methylcellulose characterized by a solution viscosity of 4.0-6.0 mPa·s.

In certain embodiments, the ASD comprises cabozantinib and one or more hydroxypropyl methylcellulose polymers. In certain embodiments, the ASD consists of cabozantinib and one or more hydroxypropyl methylcellulose polymers. In certain other embodiments, the ASD consists essentially of cabozantinib and one or more hydroxypropyl methylcellulose polymers. In any of the foregoing, a low molecular-weight hydroxypropyl methylcellulose characterized by a solution viscosity of 4.0-6.0 mPa·s may be suitable. In any of the foregoing, METHOCEL E5 may be particularly suitable.

In some embodiments, the one or more polymers comprises a hydroxypropyl cellulose ("HPC"). In certain embodiments, the one or more polymers consists of a hydroxypropyl cellulose. In certain embodiments, the one or more polymers consists essentially of a hydroxypropyl cellulose.

Hydroxypropyl cellulose is a modified cellulose obtained by reacting propylene oxide with cellulose. Hydroxypropyl cellulose is a non-ionic water-soluble cellulose ether. Hydroxypropyl cellulose also exhibits excellent solubility in a wide range of polar organic solvents.

Hydroxypropyl cellulose is available in several pharmaceutical grades from commercial vendors. For example, grades designated as HPC EF, HPC LF, and HPC JF available under the trade name KLUCEL. Certain grades having molecular weight of about 40 kDa to about 180 kDa (as measured by size exclusion chromatography) are available. These grades are characterized by a low solution viscosity (as determined at 20° C. for a 2% solution in water, according to manufacturer's specifications) of about 2 to about 20 mPa·s. The solubility of pharmaceutical grades of hydroxypropyl cellulose in aqueous media is generally insensitive to pH.

All these pharmaceutical grades may be suitable for use in the ASDs of the disclosure. A particularly suitable grade is characterized by a viscosity of about 6 to about 10 mPa·s and a molecular weight of about 140 kDa. A combination or mixture of grades of hydroxypropyl cellulose may also be employed.

In certain embodiments, the ASD comprises cabozantinib and one or more hydroxypropyl cellulose polymers. In certain embodiments, the ASD consists of cabozantinib and one or more hydroxypropyl cellulose polymers. In certain other embodiments, the ASD consists essentially of cabozantinib and one or more hydroxypropyl cellulose polymers.

In certain embodiments, the ASD comprises cabozantinib and one or more polymers or copolymers of N-vinylpyrrolidone and/or vinyl acetate. In certain embodiments, the ASD consists of cabozantinib and one or more polymers or copolymers of N-vinylpyrrolidone and/or vinyl acetate. In certain other embodiments, the ASD consists essentially of cabozantinib and one or more polymers or copolymers of N-vinylpyrrolidone and/or vinyl acetate. In any of the foregoing, vinylpyrrolidone/vinyl acetate copolymer may be particularly suitable as a copolymer of N-vinylpyrrolidone and vinyl acetate.

In some embodiments, the one or more polymers comprise a vinylpyrrolidone/vinyl acetate copolymer (also known as "copovidone" or "copolyvidone"), such as KOLLIDON VA 64, for example. Copolyvidones are non-ionic copolymers of N-vinylpyrrolidone and vinyl acetate monomers. Copolyvidones are generally soluble in hydrophilic solvents including alcoholic solvents (such as methanol, ethanol, and isopropanol), methylene chloride, glycerol, propylene glycol, and in water and other aqueous media. In aqueous media, the solubility of copolyvidone is largely pH-independent over a wide range of pH.

KOLLIDON VA 64 is a commercially available copolyvidone (BASF) derived from approximately 60% N-vinylpyrrolidone monomers and 40% vinyl acetate monomers. KOLLIDON VA 64 is characterized by a typical weight-average molecular weight in the range of 45 kDa-70 kDa (as determined by solution light scattering), and exhibits a glass transition temperature of about 101° C. (per technical literature published by BASF).

In some embodiments, the one or more polymers comprise a vinylpyrrolidone/vinyl acetate copolymer. In certain embodiments, the polymer consists of a vinylpyrrolidone/vinyl acetate copolymer. In certain embodiments, the polymer consists essentially of a vinylpyrrolidone/vinyl acetate copolymer. In the foregoing embodiments, KOLLIDON VA 64 or a similar grade of copolyvidone may suitably be employed.

In some embodiments, the ASD comprises cabozantinib and a vinylpyrrolidone/vinyl acetate copolymer. In certain embodiments, the ASD consists of cabozantinib and a vinylpyrrolidone/vinyl acetate copolymer. In certain other embodiments, the ASD consists essentially of cabozantinib and a vinylpyrrolidone/vinyl acetate copolymer. In the foregoing embodiments, KOLLIDON VA 64 or a similar grade of copolyvidone may suitably be employed.

In certain embodiments, the ASD comprises cabozantinib and one or more anionic polymers. In certain embodiments, the ASD consists of cabozantinib and one or more anionic polymers. In certain other embodiments, the ASD consists essentially of cabozantinib and one or more anionic polymers.

In certain embodiments, the ASD comprises cabozantinib and one or more anionic polymers that exhibit pH-dependent solubility. In certain embodiments, the ASD consists of cabozantinib and one or more anionic polymers that exhibit pH-dependent solubility. In certain other embodiments, the ASD consists essentially of cabozantinib and one or more anionic polymers that exhibit pH-dependent solubility. In each of the foregoing, the anionic polymers may be anionic polysaccharides and polysaccharide derivatives (such as ionizable cellulose esters), copolymers of methacrylic acid and/or alkyl acrylate, and/or derivatized vinyl acetate polymers, for example.

In certain embodiments, the ASD comprises cabozantinib and one or more ionizable cellulose esters. In certain embodiments, the ASD consists of cabozantinib and one or more ionizable cellulose esters. In certain other embodiments, the ASD consists essentially of cabozantinib and one or more ionizable cellulose esters. In any of the foregoing, the ionizable cellulose ester can be, for example, hydroxypropyl methylcellulose phthalate or hydroxypropyl methylcellulose acetate succinate.

In certain embodiments, the one or more polymers comprise HPMC-P. In certain embodiments, the polymer consists essentially of HPMC-P. In certain embodiments, the polymer consists of HPMC-P. HPMC-P is available in multiple grades, each of which demonstrates pH-dependent aqueous solubility. HPMC-P is often used as an enteric coating. It is insoluble in normal gastric fluid, but swells and partially dissolves in the higher pH environment of the upper small intestine. Generally speaking, HPMC-P is largely insoluble in an aqueous medium at pH below 5, with increased solubility in an aqueous medium at pH 5 or greater.

Two types of HPMC-P are commonly available for pharmaceutical uses, HP-50 and HP-55. The available grades of HPMC-P are differentiated by the proportion of phthalyl substituents, and the pH at which the aqueous solubility changes substantially. HP-55 is characterized by approximately 31% phthalyl substituents, and becomes more soluble above approximately pH 5.5. HP-50 is characterized by approximately 24% phthalyl substituents, and becomes more soluble above approximately pH 5.0. In the practice of the disclosure, any grade of HPMC-P may be suitable, or a mixture of two or more grades may be suitable. In certain embodiments, HP-50 is particularly suitable as the HPMC-P.

In certain embodiments, the ASD comprises cabozantinib and hydroxypropyl methylcellulose phthalate. In certain embodiments, the ASD consists essentially of cabozantinib and hydroxypropyl methylcellulose phthalate. In certain other embodiments, the ASD consists of cabozantinib and hydroxypropyl methylcellulose phthalate. In any of the foregoing, HP-50 may be particularly suitable as the HPMC-P.

In certain embodiments, the one or more polymers comprise HPMC-AS. In certain embodiments, the polymer consists of HPMC-AS. HPMC-AS is available in a variety of grades, which each demonstrate pH-dependent aqueous solubility. Generally speaking, HPMC-AS is largely insoluble in an aqueous medium at pH of 4 or lower, with increased solubility in an aqueous medium at pH 7 or greater. It is insoluble in normal gastric fluid, but swells and partially dissolves in the higher pH environment of the upper small intestine. Available grades of HPMC-AS are differentiated by the relative proportion of acetyl/succinyl substituents. Low-grade HPMC-AS comprises 5-9% acetyl substituents and 14-18% succinyl substituents; mid-grade HPMC-AS comprises 7-11% acetyl substituents and 10-14% succinyl substituents; high-grade HPMC-AS comprises 10-14% acetyl substituents and 4-8% succinyl substituents. In the practice of the disclosure, any grade of HPMC-AS may be suitable, or a mixture of two or more grades may be suitable. In certain embodiments, mid-grade HPMC-AS is particularly suitable.

In certain embodiments, the ASD comprises cabozantinib and HPMC-AS. In certain embodiments, the ASD consists essentially of cabozantinib and HPMC-AS. In certain other embodiments, the ASD consists of cabozantinib and HPMC-AS. In any of the foregoing, mid-grade HPMC-AS may be particularly suitable.

In certain embodiments, the ASD comprises cabozantinib and one or more derivatized vinyl acetate polymer. In certain embodiments, the ASD consists of cabozantinib and one or more derivatized vinyl acetate polymer. In certain other embodiments, the ASD consists essentially of cabozantinib and one or more derivatized vinyl acetate polymer.

In certain embodiments, the one or more polymers comprise polyvinyl acetate phthalate. In certain embodiments, the polymer consists of polyvinyl acetate phthalate. PVA-P demonstrates pH-dependent aqueous solubility and can be used as an enteric coating. It is insoluble in normal gastric fluid, but generally dissolves in the higher pH environment of the upper small intestine. Generally speaking, PVA-P is largely insoluble in an aqueous medium at pH below 5, with increased solubility in an aqueous medium at pH 5 or greater.

In certain embodiments, the ASD comprises cabozantinib and polyvinyl acetate phthalate. In certain embodiments, the ASD consists of cabozantinib and polyvinyl acetate phthalate. In certain other embodiments, the ASD consists essentially of cabozantinib and polyvinyl acetate phthalate.

In certain embodiments, the ASD comprises cabozantinib and one or more copolymer of methacrylic acid and/or alkyl methacrylate. In certain embodiments, the ASD consists of cabozantinib and one or more copolymer of methacrylic acid and/or alkyl methacrylate. In certain other embodiments, the ASD consists essentially of cabozantinib and one or more copolymer of methacrylic acid and/or alkyl methacrylate.

In certain embodiments, the ASD comprises cabozantinib and one or more methacrylic acid/ethyl acrylate copolymer. In certain embodiments, the ASD consists of cabozantinib and one or more methacrylic acid/ethyl acrylate copolymer. In certain other embodiments, the ASD consists essentially of cabozantinib and one or more methacrylic acid/ethyl acrylate copolymer.

In any of the foregoing, the methacrylic acid/ethyl acrylate copolymer can be EUDRAGIT L100-55, for example. EUDRAGIT L100-55 is an anionic copolymer demonstrating pH-dependent aqueous solubility. Generally speaking, EUDRAGIT L100-55 is largely insoluble in an aqueous medium at pH of 5 or lower, and largely soluble in an aqueous medium at pH 5.5 or greater. In certain embodiments, the one or more polymers comprise methacrylic acid/ethyl acrylate copolymer, such as EUDRAGIT L100-55. In certain embodiments, the polymer consists of methacrylic acid/ethyl acrylate copolymer, such as EUDRAGIT L100-55.

In any of the foregoing ASD embodiments, the cabozantinib may be present as a free base. In any of the foregoing ASD embodiments, the cabozantinib may be present as an anhydrous free base. Alternatively, in any of the foregoing ASD embodiments, the cabozantinib may be present as a malate salt. In any of the foregoing ASD embodiments, the cabozantinib may be present as an anhydrous malate salt. In particular, in any of the foregoing ASD embodiments, the cabozantinib may be present as an (S)-malate salt. In any of the foregoing ASD embodiments, the cabozantinib may be present as an anhydrous (S)-malate salt.

In certain embodiments, the ASD comprises cabozantinib free base and one or more polymers. In certain embodiments, the ASD consists of cabozantinib free base and one or more polymers. In certain other embodiments, the ASD consists essentially of cabozantinib free base and one or more polymers.

In certain embodiments, the ASD comprises anhydrous cabozantinib free base and one or more polymers. In certain embodiments, the ASD consists of anhydrous cabozantinib free base and one or more polymers. In certain other embodiments, the ASD consists essentially of anhydrous cabozantinib free base and one or more polymers.

In certain embodiments, the ASD comprises cabozantinib malate and one or more polymers. In certain embodiments, the ASD consists of cabozantinib malate and one or more polymers. In certain other embodiments, the ASD consists essentially of cabozantinib malate and one or more polymers.

In certain embodiments, the ASD comprises anhydrous cabozantinib malate and one or more polymers. In certain embodiments, the ASD consists of anhydrous cabozantinib malate and one or more polymers. In certain other embodiments, the ASD consists essentially of anhydrous cabozantinib malate and one or more polymers.

In certain embodiments, the ASD comprises cabozantinib (S)-malate and one or more polymers. In certain embodiments, the ASD consists of cabozantinib (S)-malate and one or more polymers. In certain other embodiments, the ASD consists essentially of cabozantinib (S)-malate and one or more polymers.

In certain embodiments, the ASD comprises anhydrous cabozantinib (S)-malate and one or more polymers. In certain embodiments, the ASD consists of anhydrous cabozantinib (S)-malate and one or more polymers. In certain other embodiments, the ASD consists essentially of anhydrous cabozantinib (S)-malate and one or more polymers.

The amount of cabozantinib as compared to the amount of the one or more polymers in the ASDs of the present disclosure may vary. For example, cabozantinib and the one or more polymers may be present in a w/w ratio (cabozantinib:polymer) of 20:80 to 80:20, or 25:75 to 75:25, or 30:70 to 70:30, or 35:65 to 65:35, or 40:60 to 60:40. In some embodiments, cabozantinib and the one or more polymers may be present in a ratio of 20:80, or 25:75, or 30:70, or 35:65, or 40:60, or 45:55, or 50:50, or 55:45, or 60:40, or 65:35, or 70:30, or 75:25, or 80:20.

In some embodiments, the ASD consists of cabozantinib and one or more polymers. In some embodiments, the ASD consists essentially of cabozantinib and one or more polymers. In other embodiments, the ASDs may additionally comprise one or more other pharmaceutically acceptable functional components, such as one or more antioxidants, wetting agents, or solubilizers.

Examples of antioxidants that that may be used in the ASDs of the present disclosure include, but are not limited to, acetylcysteine, ascorbyl palmitate, butylated hydroxyanisole ("BHA"), butylated hydroxytoluene ("BHT"), monothioglycerol, potassium nitrate, sodium ascorbate, sodium formaldehyde sulfoxylate, sodium metabisulfite, sodium bisulfite, vitamin E or a derivative thereof, propyl gallate, ethylenediaminetetraacetic acid ("EDTA") (e.g., disodium edetate), diethylenetriaminepentaacetic acid ("DTPA"), bismuth sodium triglycollamate, or a combination thereof. Antioxidants may also comprise amino acids such as methionine, histidine, cysteine and those carrying a charged side chain, such as arginine, lysine, aspartic acid, and glutamic acid. Any stereoisomer (e.g., l-, d-, or a combination thereof) of any particular amino acid (e.g., methionine, histidine, arginine, lysine, isoleucine, aspartic acid, tryptophan, threonine and combinations thereof) or combinations of these stereoisomers, may be present so long as the amino acid is present either in its free base form or its salt form.

The one or more antioxidants may be present in the ASD in an amount of 0.001% to 2%, or 0.01% to 1.5%, or 0.05% to 1%, or 0.1% to 0.5%, or 0.3% to 0.4%, by weight. Examples of the amount of the one or more antioxidants in the ASD include 0.001%, or 0.003%, or 0.005%, or 0.008%, or 0.01%, or 0.015%, or 0.02%, or 0.025%, or 0.03%, or 0.035%, or 0.04%, or 0.05%, or 0.075%, or 0.1%, or 0.2%, or 0.3%, or 0.4%, or 0.5%, or 0.75%, or 1.0%, or 1.5%, or 2.0%, by weight.

A variety of pharmaceutically acceptable wetting agents may be included. As a non-limiting example of a wetting agent, poloxamers, such as poloxamer 407 (e.g., PLURONIC F-127) or poloxamer 188 (e.g., PLURONIC F-68), may be suitable. Other known pharmaceutically acceptable wetting agents may be suitably employed. A wetting agent may be included in the ASD in an amount of 0.5% to 10%, or 1% to 8%, or 2% to 6%, by weight.

A variety of pharmaceutically acceptable solubilizers may be included. Non-limiting examples of suitable solubilizers include vitamin E TPGS (D-α-tocopherol polyethylene glycol succinate), SLS (sodium lauryl sulfate), and docusate sodium. A polyvinyl caprolactam-polyvinyl acetate-polyethylene glycol graft copolymer (e.g., SOLUPLUS) may also be a suitable solubilizer. Other known pharmaceutically acceptable solubilizers may be suitably employed. A solubilizer may be included in the ASD in an amount of 0.1% to 10%, or 0.25% to 5%, or 0.5 to 1%, by weight.

In some embodiments, the one or more solubilizers comprise vitamin E TPGS. In some embodiments, the one or more solubilizers consist of vitamin E TPGS. In some embodiments, the ASD is free from vitamin E TPGS. In some embodiments, the one or more solubilizers comprise polyvinyl caprolactam-polyvinyl acetate-polyethylene glycol graft copolymer. In some embodiments, the one or more solubilizers consist of polyvinyl caprolactam-polyvinyl acetate-polyethylene glycol graft copolymer. In some embodiments, the ASD is free from polyvinyl caprolactam-polyvinyl acetate-polyethylene glycol graft copolymer.

The drug load of cabozantinib in the ASDs of the present disclosure may suitably range from 20% to 80%, or 25% to 75%, or 30% to 70%, or 35% to 65%, or 40% to 60%, or 45% to 55%. As used herein, the phrase "drug load" refers to the ratio (by weight %) of cabozantinib in an ASD to the total solids weight of the ASD. By way of example, for an ASD consisting of cabozantinib and a polymer, a 1:1 w/w ratio of cabozantinib:polymer would represent a 50% drug load; a 1:2 w/w ratio of cabozantinib:polymer would represent a 33.3% drug load, etc. Examples of the drug load of cabozantinib in the ASDs include 20%, 25%, 30%, 35%, 40%, or 45%, or 50%, or 55%, or 60%, or 65%, or 70%, or 75%, or 80%.

The cabozantinib ASDs may be in the form of particles. In some embodiments, the particles do not comprise a surfactant. In other embodiments, the particles do not comprise a wetting agent. In other embodiments, the particles do not comprise a solubilizer. In other embodiments, the particles comprise neither a surfactant nor a solubilizer. In yet other embodiments, the particles are free of surfactants, wetting agents, or solubilizers. In other embodiments, the particles consist of polymer and cabozantinib, and no additional functional components.

Particles of the ASDs of the disclosure may generally comprise the shapes of spheroids. As measured by conventional light scattering or laser diffraction techniques, the diameter of the particles may range from 0.05 μm to 100 μm, or more suitably from 0.5 μm to 50 μm. The median diameter (D50 or Dv0.5) of the particle distribution may be between 1 μm and 40 μm, or between 2 μm and 25 μm, or between 3 μm and 20 μm, or between 4 μm and 15 μm, or between 5 μm and 10 μm. By way of example only, such particle size distributions can be achieved by known methods of spray drying.

In some embodiments, the median diameter of the particle distribution may be between 0.1 μm and 10 μm, or between 0.1 μm and 5 μm, or between 0.1 μm and 1 μm, or between 0.1 μm and 0.5 μm, or between 0.2 μm and 0.5 μm. By way of example only, such particle size distributions can be achieved by methods involving electrospraying, discussed further below.

Physical and Chemical Stability of ASDs

The cabozantinib ASDs of the present disclosure may demonstrate a desirable level of physical and/or chemical stability, which can be assessed by different measures. Stability is generally assessed using conventional analytical techniques commonly known in pharmaceutical sciences.

Physical and chemical stability is generally assessed after storage under controlled, elevated environmental conditions ("accelerated conditions") over a specified period of time. The storage conditions may be one or more of 25° C./60% relative humidity ("RH"), or 25° C./protected, or 30° C./65% RH, or 40° C./75% RH, or 40° C./protected, or 50° C./80% RH. (As used herein in this context, "protected" means samples were sealed in foil pouches and placed in a controlled chamber for the storage period. For example, "40° C./protected" would indicate that a sample was sealed in a foil pouch, and held in a chamber controlled at 40° C./75% RH.)

The period of time may be one or more of 1 week, or 2 weeks, or 4 weeks or 1 month, or 2 months, or 3 months, or 4 months, or 6 months, or 9 months, or 12 months, or 15 months, or 18 months, or 21 months, or 24 months, or any period of time therebetween.

The cabozantinib ASDs may demonstrate stability by having a particular assay value or a particular level of total related substances (e.g., impurities), as measured by high performance liquid chromatography (HPLC), after preparation or after storage under accelerated conditions over a specified period of time. (The terms "high performance liquid chromatography" and "HPLC" should be understood to include, but not be limited to, ultra-high performance liquid chromatography, or UHPLC, as is understood in the art.) The assay value is generally presented as a percentage of the quantity of analyte (e.g., cabozantinib) detected relative to the quantity expected, with 100% being a favorable result and large deviations from 100% being unfavorable. Generally, a reported assay value should be corrected to deduct the water content (discussed below). The total related substances is generally presented as a percentage relative to the total quantity of substances detected (i.e., analyte plus impurities), where near 0% is favorable and large deviations from 0% are unfavorable.

In some embodiments, the cabozantinib ASDs may have an assay value as measured by HPLC of at least 90%, or at least 93%, or at least 95%, or at least 97%, or at least 98%, or at least 99%, immediately after the particles are prepared.

In some embodiments, the cabozantinib ASDs may have a level of total related substances as measured by HPLC of no more than 2%, or no more than 1.5%, or no more than 1%, or no more than 0.75%, or no more than 0.5%, immediately after the particles are prepared.

In some embodiments, the cabozantinib ASDs may have an assay as measured by HPLC of at least 90%, or at least 93%, or at least 95%, or at least 97%, or at least 98%, or at least 99%, after storage at 25° C./60% RH for 1 month, or 2 months, or 3 months, or 6 months.

In some embodiments, the cabozantinib ASDs may have an assay as measured by HPLC of at least 90%, or at least 93%, or at least 95%, or at least 97%, or at least 98%, or at least 99%, after storage at 40° C./75% RH for 1 month, or 2 months, or 3 months, or 6 months.

In some embodiments, the cabozantinib ASDs may have an assay as measured by HPLC of at least 90%, or at least 93%, or at least 95%, or at least 97%, or at least 98%, or at least 99%, after storage at 40° C./protected for 1 month, or 2 months, or 3 months, or 6 months.

In some embodiments, the cabozantinib ASDs may have a level of total related substances as measured by HPLC of no more than 2%, or no more than 1.5%, or no more than 1%, or no more than 0.75%, or no more than 0.5%, after storage at 25° C./60% RH for 1 month, or 2 months, or 3 months, or 6 months.

In some embodiments, the cabozantinib ASDs may have a level of total related substances as measured by HPLC of no more than 2%, or no more than 1.5%, or no more than 1%, or no more than 0.75%, or no more than 0.5%, after storage at 40° C./75% RH for 1 month, or 2 months, or 3 months, or 6 months.

In some embodiments, the cabozantinib ASDs may have a level of total related substances as measured by HPLC of no more than 2%, or no more than 1.5%, or no more than 1%, or no more than 0.75%, or no more than 0.5%, after storage at 40° C./protected for 1 month, or 2 months, or 3 months, or 6 months.

Stability may also be assessed by evaluating changes in glass transition temperature of the cabozantinib ASDs under different storage conditions over time. Glass transition temperature can be evaluated by differential scanning calorimetry ("DSC") or modulated DSC ("mDSC") using conventional techniques. In some embodiments, the glass transition temperature as measured by DSC or mDSC does not change by more than 10° C., or more than 8° C., or no more than 6° C., or no more than 4° C., or no more than 3° C., or no more than 2° C., after storage at 25° C./60% RH for 1 month, or 2 months, or 3 months, or 6 months, or 9 months, or 12 months.

In some embodiments, the glass transition temperature as measured by DSC or mDSC does not change by more than 10° C., or more than 8° C., or no more than 6° C., or no more than 4° C., or no more than 3° C., or no more than 2° C., after storage at 40° C./75% RH for 1 month, or 2 months, or 3 months, or 6 months.

In some embodiments, the glass transition temperature as measured by DSC or mDSC does not change by more than 10° C., or more than 8° C., or no more than 6° C., or no more than 4° C., or no more than 3° C., or no more than 2° C., after storage at 40° C./protected for 1 month, or 2 months, or 3 months, or 6 months.

Stability also may be assessed by evaluating changes in crystallinity of the cabozantinib ASDs under different storage conditions over time, such as by conventional powder x-ray diffraction (PXRD) techniques. In the practice of the present disclosure, it is preferred (but not required) that the cabozantinib ASDs remain amorphous or essentially amorphous. In some embodiments, "amorphous" may be defined as having no detectable crystallinity as determined using methods known in the art, for instance, by using PXRD.

In some embodiments, "amorphous" may be defined as having a percent crystallinity no more than 5%, or no more than 4%, or no more than 3%, or no more than 2%, or no more than 1%, as determined by PXRD. In some embodiments, "essentially amorphous" may be defined as having a percent crystallinity of no more than 8%, or no more than 7%, or no more than 6%, as measured by PXRD.

The ASDs of the disclosure may be amorphous or essentially amorphous when tested promptly after preparation at t=0. For these purposes, the phrase "promptly after preparation" means that the ASD is tested within a few days after preparation, and stored under protected conditions at ambient temperature and humidity after preparation and before testing.

The ASDs may be amorphous or essentially amorphous after storage under various accelerated conditions (e.g., 25° C./60% RH, 25° C./protected, 40° C./75% RH, 40° C./protected, 50° C./80% RH, etc.) for a period of at least 1 week, or a period of at least 2 weeks, or a period of at least 3 weeks, or a period of at least 4 weeks or 1 month, or a period of at least 2 months, or a period of at least 3 months, or a period of at least 4 months, or a period of at least 5 months, or a period of at least 6 months, or a period of at least 9 months, or a period of at least 12 months or 1 year.

In some embodiments, the ASDs of the disclosure may be amorphous or essentially amorphous under conditions of high temperature and humidity (e.g., 40° C./75% RH) for a period of at least 1 month, or a period of at least 2 months, or a period of at least 3 months, or a period of at least 6 months.

The cabozantinib ASDs of the present disclosure can be characterized for water content using standard Karl Fischer coulometric titration methods. In some embodiments, the cabozantinib ASDs immediately after preparation may comprise a water content as assessed by Karl Fischer coulometric titration method of no more than 5%, or no more than 4%, or no more than 3%, or no more than 2.5%, or no more than 2%.

In some embodiments, the cabozantinib ASDs may comprise a water content as assessed by Karl Fischer coulometric titration method of no more than 10%, or no more than 7.5%, or no more than 5%, or no more than 4%, or no more than 3%, after storage at 25° C./60% RH for 1 month, or 2 months, or 3 months, or 6 months, or 9 months, or 12 months. In some embodiments, the cabozantinib ASDs may comprise a water content as assessed by Karl Fischer coulometric titration method of no more than 10%, or no more than 7.5%, or no more than 5%, or no more than 4%, or no more than 3%, after storage at 40° C./75% RH for 1 month, or 2 months, or 3 months, or 6 months, or 9 months, or 12 months. In some embodiments, the cabozantinib ASDs may comprise a water content as assessed by Karl Fischer coulometric titration method of no more than 10%, or no more than 7.5%, or no more than 5%, or no more than 4%, or no more than 3%, after storage at 40° C./protected for 1 month, or 2 months, or 3 months, or 6 months, or 9 months, or 12 months.

Methods of Making Amorphous Solid Dispersions

The cabozantinib ASDs of the present disclosure may be prepared by a variety of methods known in the art. Suitable methods generally include mixing, dissolving, or compounding the cabozantinib and the one or more polymers and, if present, one or more other functional components (such as antioxidants, wetting agents, or solubilizers) to integrate the various components. In the practice of the various methods, the cabozantinib may be introduced as cabozantinib free base, or as a salt of cabozantinib (such as cabozantinib hydrochloride), or as a solvate or hydrate of cabozantinib.

Suitable methods are generally known in the art, and include kneading, co-grinding, melting, melt extrusion, melt agglomeration, dropping, and the like. After the integration step, the material can be further processed by drying, grinding or crushing, sieving, etc.

In the practice of certain methods, cabozantinib and the one or more polymers (and other functional components, if present) may be mixed or dissolved with one or more solvents to provide a liquid feedstock. Suitable solvents may include, but are not limited to, water; an alcohol, such as ethanol, methanol, propanol or isopropanol; an ether, such as ethyl ether or methyl tert-butyl ether; acetonitrile; tetrahydrofuran or methyl tetrahydrofuran; an acetate, such as methyl acetate or ethyl acetate; a ketone, such as acetone or 2-butanone (methyl ethyl ketone); toluene; ethyl formate; 1,4-dioxane; dimethylsulfoxide; N-methyl 2-pyrrolidone; volatile halogenated solvents such as chloroform or dichloromethane; and combinations thereof. The mixing or dissolving of these contents may be by methods known in the art. For example, the contents may be mixed by manually mixing, or may be mixed with a mixing device continuously, periodically, or a combination thereof. Examples of mixing devices may include, but are not limited to, a magnetic stirrer, shaker, a paddle mixer, homogenizer, and any combination thereof.

After the cabozantinib and the one or more polymers (and other functional components, if present) are mixed, the liquid feedstock may be formed into an ASD, such as through solvent evaporation, lyophilization, precipitation or co-precipitation, spray drying, electrospraying, supercritical fluid extraction, etc. These methods are known and commonly understood in the art.

In certain embodiments of the disclosure, the liquid feedstock may be formed into an ASD through electrospraying. Electrospraying, which has also been referred to as electrohydrodynamic atomization, has been used to produce ASD particles on a micron or sub-micron scale from suitable liquid feedstocks. Electrospraying may be particularly suitable for forming ASDs using cabozantinib free base.

In one suitable electrospraying technique, the liquid feedstock is emitted through one or more nozzles toward a substrate in the presence of an electric potential applied between the nozzles and the substrate. The liquid feedstock experiences electrical shear stress due to the applied potential. When the shear stress overcomes the surface tension of the liquid feedstock, droplets are emitted from the tips of the nozzles.

Conditions are controlled such that a cone jet of droplets is emitted at the tip of the nozzles. The droplets take on an electric charge and repel one another, which prevents their coagulation and promotes self-dispersion. The charged droplets accelerate toward the substrate as a result of the applied electric field.

During the short flight path, the solvent "flashes off" from the charged droplets. This fast evaporation creates a situation in which the charged droplets shrink in size but increase in charge density. At a critical limit, the droplets will break up into yet smaller droplets. An essentially monodisperse population of fine droplets is ultimately produced. The size of the droplets can range from sub-micron to several microns.

The essentially complete evaporation of solvent from the charged droplets results in the formation of relatively uniform particles of the non-volatile components from the liquid feedstock. The evaporation process occurs at a time-scale that does not permit crystallization of the non-volatile components. Additionally, evaporative cooling associated with the extremely rapid solvent evaporation contributes a quenching effect to preserve the particles in an amorphous state. Furthermore, electrospray conditions can be selected and the system can be configured such that the amorphous particles contain little residual solvent.

In some embodiments of the disclosure, the liquid feedstock may be formed into an ASD using electrospray techniques and/or devices. Suitable methods and equipment are described, for example, in U.S. Pat. Nos. 6,746,869, 6,764,720, 7,279,322, 7,498,063, 7,951,428, 7,972,661, 8,992,603, 9,040,816, 9,050,611, 9,108,217, 9,642,694, 10,562,048, U.S. Patent Publication No. 2014-0158787, U.S. Patent Publication No. 2015-0190253, U.S. Patent Publication No. 2016-0038968, U.S. Patent Publication No. 2016-0175881, U.S. Patent Publication No. 2016-0235677, U.S. Patent Publication No. 2019-0193109, and U.S. Patent Publication No. 2020-0179963.

As noted above, by using an electrospray technique, the median diameter of the cabozantinib ASD particle distribution may be between 0.1 μm and 10 μm, or between 0.2 μm and 5 μm, or between 0.5 μm and 2 μm. It should further be noted that the cabozantinib in the amorphous particles is generally not considered to be solvated. Even where the liquid feedstock may have been prepared using a solvate or hydrate form of cabozantinib, the solvate or hydrate is understood to flash off with the other solvents, and the electrosprayed amorphous particles comprise non-solvated cabozantinib (such as anhydrous cabozantinib).

In some embodiments, the electrospray technique may be performed at room temperature. In certain embodiments, no heated air is used. In other embodiments, the liquid feedstock is held at an elevated temperature during the electrospray process.

In some embodiments, the electrospray technique may be performed using one or more capillary nozzles. In certain embodiments, the electrospray technique does not use pneumatic nozzles such as nozzles that rely on kinetic energy; pressure nozzles; rotary nozzles such as or nozzles that rely on centrifugal energy; or ultrasonic nozzles such as nozzles that rely on acoustic energy. In some embodiments, the electrospray technique generates a yield of over 85%, or over 90%, or over 95%, or over 98%.

In certain embodiments, the liquid feedstock may be formed into an ASD through spray drying. Spray drying is suitable for forming ASDs using cabozantinib free base or salt forms of cabozantinib. Generally speaking, spray drying involves the atomization of a liquid feedstock into very small droplets within a hot drying gas. The feedstock is pumped or otherwise propelled through a nozzle or other atomizing apparatus to form droplets within a drying chamber. Within the drying chamber, the droplets are exposed to an environment of the heated drying gas (usually flowing air or nitrogen), leading to flash drying of the droplets (by evaporative removal of solvent) and resultant production of solid particles. The dried particles are collected, generally at an output port in the drying chamber.

Various apparatus and methods of spray drying may be employed to form an ASD of the disclosure. In the practice of the present disclosure, the median diameter of the ASD particle distribution achieved by spray drying may be generally between 1 μm and 80 μm, more commonly between 1 μm and 40 μm, or between 2 μm and 25 μm, or between 3 μm and 20 μm, or between 4 μm and 15 μm, or between 5 μm and 10 μm.

In some embodiments, the process for forming an ASD does not require a secondary drying step, i.e., a drying step that occurs after the particles are produced. In other embodiments, a secondary drying step is employed to further remove most or all of the residual solvents. The secondary drying step can be done under suitable conditions (such as elevated temperature) that allow for the removal of solvent but do not result in the recrystallization of the cabozantinib. For example, a secondary drying step can be done at a temperature below a glass transition temperature. A secondary drying step can also be done at reduced pressure. A combination of elevated temperature and reduced pressure can also be used for a secondary drying step.

Pharmaceutical Compositions

An aspect of the present disclosure relates to pharmaceutical compositions comprising a cabozantinib ASD. The pharmaceutical compositions generally comprise cabozantinib ASD and one or more pharmaceutically acceptable excipients. The pharmaceutical compositions of the present disclosure may be in a dosage form appropriate for oral administration. In some embodiments, the pharmaceutical compositions may be in the form of granules, or may be prepared as granules as an intermediate step to forming another oral dosage form, such as tablets, sprinkles, or pellets. In some embodiments, the pharmaceutical compositions may be in a solid dosage form for oral administration, such as a capsule, tablet, sprinkle, or pellet. In other embodiments, the pharmaceutical composition may suitably be in the form of an aqueous or nonaqueous suspension or solution. Such compositions may be prepared using known excipients and known preparation methods.

Information regarding suitable excipients, and commercial sources therefor, can be found in Sheskey P J (ed.) *Handbook of Pharmaceutical Excipients, 9$^{th}$ Ed.* London: Pharmaceutical Press; 2020 (ISBN 0857113755); alternatively, the most up-to-date edition of the same title may be consulted.

The pharmaceutical compositions of the present disclosure may demonstrate a desirable level of physical and/or chemical stability over some suitable period of time, and optionally under accelerated conditions. The stability of the pharmaceutical compositions can be assessed by different measures. For instance, the pharmaceutical compositions may demonstrate chemical stability by having a particular assay value or a particular level of total related substances (e.g., impurities, degradation products, and the like), measured after storage under accelerated conditions over a specified period of time. In some embodiments, the pharmaceutical compositions may be amorphous as assessed using PXRD (i.e., no crystalline character detected) after storage under the specified conditions.

In some embodiments, the pharmaceutical compositions may be substantially amorphous as assessed using PXRD, after storage under the specified conditions. The storage conditions may be one or more of 25° C./60% RH, or 30° C./65% RH, or 40° C./75% RH. The period of time may be one or more of 1 week, or 2 weeks, or 1 month, or 2 months, or 3 months, or 4 months, or 6 months, or 9 months, or 12 months, or 15 months, or 18 months, or 21 months, or 24 months, or any period of time therebetween.

Suspension/Solution.

A pharmaceutical composition may be in the form of an aqueous or nonaqueous suspension or solution. Such compositions may be prepared using known excipients and known preparation methods. Such compositions may comprise a cabozantinib ASD of the present disclosure and one or more suitable pharmaceutically acceptable carriers, along with optional excipients, such as one or more solubilizers, one or more buffering agent(s), one or more pH-adjusting agents, one or more surfactants, and/or one or more antioxidants.

Carriers that that may be used in the pharmaceutical compositions of the present disclosure include, but are not limited to, water, salt solutions (e.g., Ringer's solution and the like), alcohols, oils, gelatins, and carbohydrates such as lactose, amylose or starch, fatty acid esters, methylcellulose, hydroxyethylcellulose, hydroxypropyl cellulose, polyvinyl pyrrolidine, and mixtures or solutions including any of the foregoing. The carrier may be used in combination with a buffering agent.

In some embodiments, the composition of the present disclosure may comprise a carrier at a pH from 5 to 9, or from 6 to 8. In certain embodiments, the composition may comprise a carrier having a neutral pH. In certain embodiments, the pH of the carrier may be at or near physiological pH.

Solubilizers that may be used in the pharmaceutical compositions of the present disclosure include, but are not limited to, polyvinyl caprolactam-polyvinyl acetate-polyethylene glycol copolymer (SOLUPLUS), d-α-tocopherol acid polyethylene glycol (PEG) 1000 succinate (TPGS), PEG-40 hydrogenated castor oil (CREMOPHOR RH40), PEG-35 castor oil (CREMOPHOR EL), PEG-40 stearate (MYRJ 540), hard fat (such as GELUCIRE 33/01), polyoxylglycerides (such as GELUCIRE 44/14), stearoyl polyoxylglycerides (such as GELUCIRE 50/13), PEG-8 caprylic/capric glycerides (such as LABRASOL) and poloxamers (such as PLURONIC, KOLLIPHOR).

Buffering agents that that may be used in the pharmaceutical compositions of the present disclosure include, but are not limited to, triethylamine, meglumine, diethanolamine, ammonium acetate, arginine, lysine, histidine, a phosphate buffer (e.g., sodium phosphate tribasic, sodium phosphate dibasic, sodium phosphate monobasic, or o-phosphoric acid), sodium bicarbonate, a Britton-Robinson buffer, a Tris buffer (containing Tris(hydroxymethyl)-aminomethane), a HEPES buffer (containing N-(2-hydroxyethyl)piperazine-N'-(2-ethanesulfonic acid), acetate, a citrate buffer (e.g., citric acid, citric acid anhydrous, citrate monobasic, citrate dibasic, citrate tribasic, citrate salt), ascorbate, glycine, glutamate, lactate, malate, formate, sulfate, and mixtures thereof.

Further, pH-adjusting agents that that may be used in the pharmaceutical compositions of the present disclosure include pharmaceutically acceptable acids or bases. For example, acids may include, but are not limited to, one or more inorganic mineral acids such as hydrochloric, hydrobromic, sulfuric, phosphoric, nitric, and the like; or one or more organic acids such as acetic, succinic, tartaric, ascorbic, citric, glutamic, benzoic, methanesulfonic, ethanesulfonic, trifluoroacetic, and the like. The bases may be one or more inorganic bases or organic bases, including, but not limited to, alkaline carbonate, alkaline bicarbonate, alkaline earth metal carbonate, alkaline hydroxide, alkaline earth metal hydroxide, or amine. For example, the inorganic or organic base may be an alkaline hydroxide such as lithium hydroxide, potassium hydroxide, cesium hydroxide, sodium hydroxide, or the like; an alkaline carbonate such as calcium carbonate, sodium carbonate, or the like; or an alkaline bicarbonate such as sodium bicarbonate, or the like; the organic base may also be sodium acetate.

Surfactants that that may be used in the pharmaceutical compositions of the present disclosure may include, but are not limited to, sodium lauryl sulfate, docusate sodium, dioctyl sodium sulfosuccinate, dioctyl sodium sulfonate, benzalkonium chloride, benzethonium chloride, lauromacrogol 400, polyoxyl 40 stearate, polyoxyethylene hydrogenated castor oil (e.g., polyoxyethylene hydrogenated castor oil 10, 50, or 60), glycerol monostearate, polysorbate (e.g., polysorbate 40, 60, 65, or 80), sucrose fatty acid ester, methyl cellulose, polyalcohols and ethoxylated polyalcohols, thiols (e.g., mercaptans) and derivatives, poloxamers, polyethylene glycol-fatty acid esters (e.g., KOLLIPHORRH40, KOLLIPHOR EL), lecithins, and mixtures thereof.

Antioxidants that that may be used in the pharmaceutical compositions of the present disclosure include, but are not limited to, acetylcysteine, ascorbyl palmitate, BHA, BHT, monothioglycerol, potassium nitrate, sodium ascorbate, sodium formaldehyde sulfoxylate, sodium metabisulfite, sodium bisulfate, vitamin E or a derivative thereof, propyl gallate, EDTA (e.g., disodium edetate), DTPA, bismuth sodium triglycollamate, or a combination thereof. Antioxidants may also comprise amino acids such as methionine, histidine, cysteine and those carrying a charged side chain, such as arginine, lysine, aspartic acid, and glutamic acid. Any stereoisomer (e.g., l-, d-, or a combination thereof) of any particular amino acid (e.g., methionine, histidine, arginine, lysine, isoleucine, aspartic acid, tryptophan, threonine and combinations thereof) or combinations of these stereoisomers, may be present so long as the amino acid is present either in its free base form or its salt form.

In some embodiments, the pharmaceutical compositions of the present disclosure may include other suitable pharmaceutical additives such tonicity-adjusting agents, preservatives, emulsifiers, sweeteners, flavoring agents, suspending agents, thickening agents, colors, viscosity regulators, stabilizers, and osmo-regulators.

A suspension or solution according to the present disclosure may be prepared using methods known in the art. For example, the cabozantinib ASD and the one or more pharmaceutically acceptable excipients may be mixed by simple mixing, or may be mixed with a mixing device continuously, periodically, or a combination thereof. Examples of mixing devices may include, but are not limited to, a magnetic stirrer, shaker, a paddle mixer, homogenizer, and any combination thereof.

Solid Dosage Forms.

In some embodiments, the pharmaceutical compositions may be in a solid dosage form for oral administration, such as a capsule, tablet, sprinkle, or pellet. In particular, in one aspect the present disclosure provides a pharmaceutical composition in the form of a tablet. In some embodiments, the pharmaceutical compositions may be in the form of granules, or may be prepared as granules as an intermediate step to forming another oral dosage form, such as tablets, sprinkles, or pellets.

The solid oral dosage form pharmaceutical compositions comprise a cabozantinib ASD and one or more pharmaceutically acceptable excipients, such as one or more fillers, one or more disintegrants, and/or other optional excipients such as one or more binders, one or more lubricants, one or more wetting agents, one or more solubilizers, one or more surfactants, one or more antioxidants, and/or one or more glidants, for example.

Suitable fillers include acacia, calcium carbonate, calcium sulfate, calcium sulfate dihydrate, compressible sugar, dibasic calcium phosphate anhydrous (e.g., FUJICALIN, EMCOMPRESS), dibasic calcium phosphate dihydrate, tribasic calcium phosphate, monobasic sodium phosphate, dibasic sodium phosphate, lactose monohydrate, lactose anhydrous, magnesium oxide, magnesium carbonate, silicon dioxide, magnesium aluminum silicate, maltodextrin, mannitol, methyl cellulose, microcrystalline cellulose (e.g., AVICEL PH-101, AVICEL PH-102, AVICEL PH-105), powdered cellulose, starches, sorbitol, dextrose, dextrates, dextrin, sucrose, xylitol and mixtures thereof.

One or more disintegrants may be included. Suitable disintegrants in the practice of the disclosure include natural, modified or pre-gelatinized starch, sodium starch glycolate, sodium carboxymethyl cellulose, calcium carboxymethyl cellulose, croscarmellose sodium, crospovidone, polyvinylpolypyrrolidone, and mixtures thereof.

Suitable binders include various celluloses and cross-linked polyvinylpyrrolidone, microcrystalline cellulose (e.g., AVICEL PH-101, AVICEL PH-102, AVICEL PH-105), or silicified microcrystalline cellulose (e.g., PROSOLV SMCC), for example.

One or more lubricants may be included to reduce friction with and adherence to processing equipment during processing and tableting. Examples of lubricants known in the art include, but are not limited to, magnesium stearate, calcium stearate, zinc stearate, stearic acid, stearyl alcohol, glyceryl monostearate, sodium stearyl fumarate, talc, glyceryl behenate, sodium benzoate, sodium lauryl sulfate, and the like.

Solubilizers that may be optionally included in the pharmaceutical compositions of the present disclosure include, but are not limited to, polyvinyl caprolactam-polyvinyl acetate-polyethylene glycol copolymer (SOLUPLUS), d-α-tocopherol acid polyethylene glycol (PEG) 1000 succinate (TPGS), PEG-40 hydrogenated castor oil (CREMOPHOR RH40), PEG-35 castor oil (CREMOPHOR EL), PEG-40 stearate (MYRJ 540), hard fat (such as GELUCIRE 33/01), polyoxylglycerides (such as GELUCIRE 44/14), stearoyl polyoxylglycerides (such as GELUCIRE 50/13), PEG-8 caprylic/capric glycerides (such as LABRASOL) and poloxamers (such as PLURONIC, KOLLIPHOR).

In some embodiments, the pharmaceutical compositions may comprise a cabozantinib ASD and one or more pharmaceutically acceptable excipients, with the proviso that the pharmaceutically acceptable excipients do not comprise polyvinyl caprolactam-polyvinyl acetate-polyethylene glycol graft co-polymer (e.g., SOLUPLUS).

Surfactants that may be optionally included in the pharmaceutical compositions of the present disclosure may include, but are not limited to, sodium lauryl sulfate, docusate sodium, dioctyl sodium sulfosuccinate, dioctyl sodium sulfonate, benzalkonium chloride, benzethonium chloride, lauromacrogol 400, polyoxyl 40 stearate, polyoxyethylene hydrogenated castor oil (e.g., polyoxyethylene hydrogenated castor oil 10, 50, or 60), glycerol monostearate, polysorbate (e.g., polysorbate 40, 60, 65 or 80), sucrose fatty acid ester, methyl cellulose, polyalcohols and ethoxylated polyalcohols, thiols (e.g., mercaptans) and derivatives, poloxamers, polyethylene glycol-fatty acid esters (e.g., KOLLIPHOR RH40, KOLLIPHOR EL), lecithins, and mixtures thereof.

A variety of pharmaceutically acceptable wetting agents may be included. As a non-limiting example of a wetting agent, poloxamers, such as poloxamer 407 (e.g., PLURONIC F-127) or poloxamer 188 (e.g., PLURONIC F-68), may be suitable. Other known pharmaceutically acceptable wetting agents may be suitably employed. A wetting agent may be included in the ASD in an amount of 0.5% to 10%, or 1% to 8%, or 2% to 6%, by weight.

Antioxidants that may be optionally included in the pharmaceutical compositions of the present disclosure include, but are not limited to, acetylcysteine, ascorbyl palmitate, BHA, BHT, monothioglycerol, potassium nitrate, sodium ascorbate, sodium formaldehyde sulfoxylate, sodium metabisulfite, sodium bisulfate, vitamin E or a derivative thereof, propyl gallate, EDTA (e.g., disodium edetate), DTPA, bismuth sodium triglycollamate, or a combination thereof.

Glidants are employed to improve flow properties of a powder or granule mixture prior to prior to further processing (such as tablet compression, for example). Suitable glidants that may be employed in the present disclosure include, but are not limited to, colloidal silica (e.g., hydrophobic colloidal silica, such as AEROSIL), silica gel, precipitated silica, and the like.

Granules.

In some embodiments, the pharmaceutical compositions may be in the form of granules. In other embodiments, granules may be prepared as an intermediate step to forming another oral dosage form, such as a tablet or pellet, or as a fill for a capsule. Granules typically have improved flow, handling, blending, and compression properties relative to ungranulated materials.

The granules may be prepared using the ASD particles by processes known in the art, including wet granulation and dry granulation. In some embodiments, a granule blend is formed by dry-blending granule components, and then the granule blend is densified using a roller compactor which typically forms ribbons of material. The ribbons are then reduced in size by milling to form granules.

Wet granulation techniques may also be employed to form granules, provided the solvents and process selected do not alter the properties of the ASD. Improved wetting, disintegrating, dispersing and dissolution properties may be obtained by the inclusion of suitable excipients, as described above.

In some embodiments, the granule blend (and accordingly the resulting granules) can include some or all of the components of a desired tablet formulation. After granulation, the granules can be incorporated into a tableting blend and compressed into tablets, as described below.

Accordingly, in another aspect, the present disclosure provides a pharmaceutical composition in the form of granules comprising ASD particles. In another aspect, the present disclosure provides a pharmaceutical composition comprising granules that include ASD particles.

In certain embodiments, the granules may comprise the ASD in an amount of 20% to 80% by weight of the granule; one or more granulation fillers in an amount of 20% to 80% by weight of the granule; one or more granulation disintegrants in an amount of 1% to 15% by weight of the granule; and optionally one or more solubilizers in an amount of 2% to 20% by weight of the granule; and optionally one or more lubricants in an amount of 0.2% to 5% by weight of the granule; and optionally one or more glidants in an amount of 0.2% to 5% by weight of the granule.

In some embodiments, a solubilizer may be included in the granules. A variety of pharmaceutically acceptable solubilizers may be included. As a non-limiting example of a suitable solubilizer, poloxamers, such as poloxamer 407 (e.g., PLURONIC F-127) or poloxamer 188 (e.g., PLURONIC F-68), may be included. Other known pharmaceutically acceptable solubilizers may be suitably employed. A solubilizer may be included in the granules in an amount of 0.5% to 10%, or 1% to 10%, or 3% to 8%, or 5%, by weight of the granules.

Tablets.

In another aspect, the present disclosure provides a pharmaceutical composition in the form of a tablet. The tablet of the disclosure comprises a cabozantinib ASD and one or more pharmaceutically acceptable excipients, such as one or more fillers, one or more disintegrants, and/or other optional excipients such as one or more binders, one or more lubricants, one or more wetting agents, one or more solubilizers, one or more surfactants, one or more antioxidants, and/or one or more glidants, for example.

In certain embodiments, the tablet may comprise the ASD in an amount of 10% to 90% by weight of the tablet; one or more fillers in an amount of 5% to 90% by weight of the tablet; one or more disintegrants in an amount of 1% to 15% by weight of the tablet; one or more lubricants and/or glidants in an amount of 0.1% to 5% by weight of the tablet; one or more binders in an amount of 1% to 10% by weight of the tablet.

The tablet may comprise 10% to 90% of the cabozantinib ASD, based on the weight of the tablet. In some embodiments, the tablet comprises 15% to 80% of the cabozantinib ASD. In other embodiments, the tablet comprises 20% to 75% of the cabozantinib ASD. In other embodiments, the tablet comprises 25% to 70% of the cabozantinib ASD.

Generally, the tablet may comprise from 5% to 90% of the one or more fillers, by weight of the tablet. Suitable fillers are described above. In some embodiments, the tablet comprises 10% to 80% of the one or more fillers. In other embodiments, the tablet comprises 15% to 70% of the one or more fillers. In yet other embodiments, the tablet comprises 20% to 65% of the one or more fillers.

Generally, the tablet may comprise from 1% to 15% of one or more disintegrants, by weight of the tablet. Suitable disintegrants are described above. In some embodiments, the tablet will comprise from 2% to 15% of the one or more disintegrants. In other embodiments, the tablet will comprise from 5% to 10% of the one or more disintegrants.

Generally, the tablet may comprise from 1% to 10% of one or more binders by weight of the tablet. Suitable binders are described above.

One or more lubricants can optionally be included in the tablet. Suitable lubricants are described above. When included, the one or more lubricant is generally present in the range of 0.1% to 5%, by weight of the tablet. In some embodiments, the one or more lubricant is generally present in the range of 0.25% to 2%, by weight of the tablet.

When included, the one or more antioxidant is generally present in the range of 0.05% to 2%, by weight of the tablet.

In some embodiments, the one or more antioxidant is generally present in the range of 0.1% to 0.5%, by weight of the tablet.

One or more glidants can optionally be included in the tablet. Suitable glidants are described above. When included, the one or more glidant is generally present in the range of 0.1% to 5%, by weight of the tablet. In some embodiments, the one or more glidant is generally present in the range of 0.25% to 2%, by weight of the tablet.

As described above, in some embodiments, it may be desirable to form granules as an intermediate step to forming a tableting blend. In another aspect, the present disclosure provides a pharmaceutical composition in the form of tablets which comprise granules that include ASD particles.

In some embodiments, the tablets of the disclosure include granules as described above, along with additional excipients external to the granules ("extra-granular excipients"). In one embodiment, the tablet comprises from 10% to 90% of the granules, by weight of the tablet; and 10% to 90% of the extra-granular excipients, by weight of the tablet. In certain embodiments, the tablet comprises from 20% to 80% of the granules, by weight of the tablet; and 20% to 80% of the extra-granular excipients, by weight of the tablet. In yet other embodiments, the tablet comprises from 30% to 70% of the granules, by weight of the tablet; and 30% to 70% of the extra-granular excipients, by weight of the tablet.

By way of example, the extra-granular excipients could include one or more tablet fillers and/or one or more tablet disintegrants. Suitable fillers and disintegrants are described above.

In addition, the extra-granular excipients could include one or more solubilizers, one or more lubricants and/or one or more glidants. Suitable solubilizers, lubricants and glidants are described above.

Pharmaceutical compositions of the disclosure in the form of a tablet may be prepared using methods known in the art. For example, the cabozantinib ASD and the one or more pharmaceutically acceptable excipients may be blended to provide a tableting blend by hand or bag blending, or using a suitable device. Examples of suitable blending devices may include, but are not limited to, a tumble blender, v-blender, acoustic blender, paddle mixer, screw mixer, and the like.

Suitable tableting blends may then be compressed into tablets weighing from 100 to 1000 mg using, for example, a manual tablet press or a conventional mechanical tablet press. In the case of tablets, compression force must be carefully selected to achieve desired mechanical properties of the tablet without compromising performance. If too high a compression force is used, the porosity of the tablet decreases, which can slow the rate of water wicking into the tablet, and can undesirably result in degraded dissolution performance.

Treatment of Proliferative Disorders

Aspects of the present disclosure relate to uses of the cabozantinib ASDs of the present disclosure, or pharmaceutical compositions comprising the ASDs. In the practice of such embodiments of the present disclosure, cabozantinib ASDs and pharmaceutical compositions may be suitably administered to subjects or to patients (i.e., persons being treated for a disease or condition).

In some embodiments, the cabozantinib ASD or pharmaceutical composition is administered to a subject. The subject in the methods of the present disclosure may be a mammal, which includes, but is not limited to, a human, monkey, cow, hog, sheep, horse, dog, cat, rabbit, rat, and mouse. In certain embodiments, the subject is a human. As used herein, the phrase "healthy human subject" means a human that is generally healthy and is not being treated for the disease or condition for which the pharmaceutically active component (e.g., cabozantinib) is generally used for therapy. Selection of suitable healthy human subjects for pharmacokinetic assessment is within the expertise of one skilled in the art of clinical trial design.

In other embodiments, the cabozantinib ASD or pharmaceutical composition is administered to a human patient. The human patient may be adult or of a pediatric age, e.g., younger than 17 years old. In certain embodiments, the human patient is 1 year of age or older. As used herein, a "patient" is a subject, particularly a human, who is being treated for a disease or condition for which the pharmaceutically active component (e.g., cabozantinib) is generally used for therapy.

An aspect of the present disclosure relates to the use of the cabozantinib ASDs of the present disclosure or pharmaceutical compositions of the present disclosure to treat a proliferative disorder. Some embodiments relate to a method of treating a proliferative disorder, the method comprising administering an ASD of the present disclosure, or a pharmaceutical composition of the present disclosure, to a patient in need thereof. Some embodiments relate to a use of a cabozantinib ASD or a pharmaceutical composition of the present disclosure for treating a proliferative disorder in a patient in need thereof, the use comprising administering the cabozantinib ASD or pharmaceutical composition to the patient. Some embodiments relate to a cabozantinib ASD or a pharmaceutical composition of the present disclosure for use in treating a proliferative disorder in a patient in need thereof, the use comprising administering the cabozantinib ASD or the pharmaceutical composition to the patient. Some embodiments relate to a use of a cabozantinib ASD or pharmaceutical composition of the present disclosure in the manufacture of a medicament for treating a proliferative disorder.

In one aspect, the present disclosure relates to a method of treating a proliferative disorder in a patient in need thereof, the method comprising administering a therapeutically effective amount of an ASD of the present disclosure or of a pharmaceutical composition of the present disclosure to the patient.

The proliferative disorder may be cancer. Examples of such proliferative disorders may include, but are not limited to, leukemias such as acute lymphocytic leukemia (or acute lymphoblastic leukemia), acute myeloid leukemia (or acute myelogenous leukemia), chronic lymphocytic leukemia (or chronic lymphoblastic leukemia), chronic myeloid leukemia (or chronic myelogenous leukemia); age-related macular degeneration and diabetic retinopathy, anal and oral cancers, angiosarcoma, basal cell carcinoma and squamous cell carcinoma, bladder cancer, brain cancer, breast cancer, cancer of the central nervous system, cervical, cervix uteri cancer, choriocarcinoma, colon cancer, gastrointestinal stromal tumor, corpus uteri cancer, esophageal cancer, Ewing's Sarcoma, eye or ocular cancer, head and neck cancer, hemangioendothelioma, hemangiomas and lymphangiogenesis, Kaposi's Sarcoma, larynx cancer, liver cancer, lung cancer, lymphoma, mouth/pharynx cancer, multiple myeloma; cardiac hypertrophy, neuroblastoma, neurofibromatosis, ovary cancer, pancreatic cancer, prostate cancer, rectal cancer, renal cancer, rhabdomyosarcoma, skin melanoma, small cell lung cancer, stomach cancer, testis cancer, throat cancer, tuberous sclerosis, and Wilms Tumor.

In certain embodiments, the proliferative disorder may be renal cell carcinoma (RCC). In certain embodiments, the proliferative disorder may be hepatocellular carcinoma (HCC). In certain embodiments, the proliferative disorder may be differentiated thyroid cancer (DTC). In some embodiments, the proliferative disorder may be medullary thyroid cancer (MTC).

In the methods and uses of the present disclosure, a therapeutically effective amount of the cabozantinib ASD or the pharmaceutical composition of the present disclosure will be based on, among other factors, the route of administration, the age and size of the patient, and the proliferative disorder being treated. As used herein, the term "therapeutically effective amount" means that amount that is expected to elicit the biological or medical response that is being sought by a clinician.

In some embodiments, a therapeutically effective amount may be 0.05 to 5 mg/kg/day, or 0.1 to 3 mg/kg/day, or 0.2 to 2 mg/kg/day of cabozantinib. In other embodiments, a therapeutically effective amount may be fixed dose. For instance, the fixed dose may be 5 mg to 200 mg, or 10 mg to 180 mg, or 20 mg to 160 mg, per day of cabozantinib. In certain embodiments, the fixed dose may be 10 mg, or 20 mg, or 25 mg, or 30 mg, or 40 mg, or 50 mg, or 60 mg, or 70 mg, or 75 mg, or 80 mg, or 90 mg, or 100 mg, or 110 mg, or 120 mg, or 125 mg, or 130 mg, or 140 mg, or 150 mg, or 160 mg, or 170 mg, or 175 mg, or 180 mg, or 190 mg, or 200 mg, per day of cabozantinib. The fixed dose will depend on the specific disorder being treated. Depending on the treatment regimen, the quantity of cabozantinib dosed per day may be dosed all at once (once-daily dosing), or may be divided and dosed more frequently (such as twice-per-day dosing).

As described further below, pharmaceutical compositions of the present disclosure may provide enhanced or otherwise desirable bioavailability under a variety of administration conditions. The term "bioavailability" refers to the rate and extent to which an active ingredient is absorbed from a pharmaceutical composition and becomes available at the site of action. In the case of orally administered pharmaceuticals, bioavailability is generally assessed by monitoring a subject's blood plasma over time for the presence of an active ingredient (or suitable surrogate, such as a metabolite) after administration of a pharmaceutical composition, to evaluate the pharmacokinetic profile.

From the pharmacokinetic profile, certain relevant pharmacokinetic parameters can be established. Such pharmacokinetic parameters can include $C_{max}$, $T_{max}$, and/or AUC, for example. $C_{max}$ indicates the maximum observed plasma concentration over the observed time period. $T_{max}$ indicates the time point at which the maximum plasma concentration is observed.

AUC indicates the numerical area-under-the-curve ("AUC") for the concentration-time curve, and can be assessed for a specified time interval 0–t, denoted as $AUC_{0\text{-}t}$ (alternatively denoted as $AUC_t$). $AUC_{0\text{-}t}$ is generally obtained by numerical integration of the concentration-time curve over the period t=0 to the time "t" (e.g., $AUC_{0\text{-}24\ h}$ or $AUC_{24\ h}$ indicates the integral over the time period from t=0 to t=24 hours). $AUC_{0\text{-}last}$ (alternatively denoted as $AUC_{last}$) indicates the integral from t=0 to the last time point sampled in the observed time period. $AUC_{0\text{-}inf}$ (alternatively denoted as $AUC_{inf}$) indicates the integral from t=0 to t="infinity," which is determined by extrapolation of obtained data using commonly employed pharmacokinetic statistical modeling techniques.

Typically, plasma concentration data is log-transformed for analysis. For most pharmacokinetic analyses, data for a number of test subjects is pooled for analysis. When data is pooled, the relevant pharmacokinetic parameters may be expressed as a population geometric mean, in accordance with conventional pharmacokinetic statistical analyses and methods.

Administration of an ASD or pharmaceutical composition of the present disclosure can be characterized by the pharmacokinetic profile, or by the observed or calculated pharmacokinetic parameters resulting from the administration of the ASD or pharmaceutical composition at certain dosages to a subject or patient, under stated administration conditions.

Embodiments of the Disclosure Include

Embodiment ASD1 is an amorphous solid dispersion comprising cabozantinib and one or more polymers. Embodiment ASD2 is an amorphous solid dispersion comprising cabozantinib free base and one or more polymers. Embodiment ASD3 is an amorphous solid dispersion comprising anhydrous cabozantinib free base and one or more polymers. Embodiment ASD4 is an amorphous solid dispersion comprising a salt of cabozantinib and one or more polymers. Embodiment ASD5 is an amorphous solid dispersion comprising a malate salt of cabozantinib and one or more polymers. Embodiment ASD6 is an amorphous solid dispersion comprising cabozantinib (S)-malate and one or more polymers.

Embodiment ASD7 is an amorphous solid dispersion according to any of Embodiments ASD1 to ASD6, wherein the cabozantinib and the one or more polymers are present in the amorphous solid dispersion in a w/w ratio of 20:80 to 80:20 (cabozantinib:polymer). Embodiment ASD8 is an amorphous solid dispersion according to any of Embodiments ASD1 to ASD6, wherein the cabozantinib and the one or more polymers are present in the amorphous solid dispersion in a w/w ratio of 30:70 to 70:30 (cabozantinib: polymer). Embodiment ASD9 is an amorphous solid dispersion according to any of Embodiments ASD1 to ASD6, wherein the cabozantinib and the one or more polymers are present in the amorphous solid dispersion in a w/w ratio of 40:60 to 60:40 (cabozantinib:polymer). Embodiment ASD10 is an amorphous solid dispersion according to any of Embodiments ASD1 to ASD6, wherein the cabozantinib and the one or more polymers are present in the amorphous solid dispersion in a w/w ratio of 50:50 (cabozantinib:polymer).

Embodiment ASD11 is the amorphous solid dispersion according to any of Embodiments ASD1 to ASD10 wherein the amorphous solid dispersion consists essentially of cabozantinib and the one or more polymers. Embodiment ASD12 is the amorphous solid dispersion according to any of Embodiments ASD1 to ASD10 wherein the amorphous solid dispersion consists of cabozantinib and the one or more polymers.

Embodiment ASD13 is an amorphous solid dispersion according to any of Embodiments ASD1 to ASD12, wherein the one or more polymers includes an ionizable polymer. Embodiment ASD14 is an amorphous solid dispersion according to any of Embodiments ASD1 to ASD13, consisting of cabozantinib and one or more ionizable polymers. Embodiment ASD15 is an amorphous solid dispersion according to any of Embodiments ASD1 to ASD13, consisting essentially of cabozantinib and one or more ionizable polymers.

Embodiment ASD16 is an amorphous solid dispersion according to any of Embodiments ASD1 to ASD12, comprising cabozantinib and one or more anionic polymers. Embodiment ASD17 is an amorphous solid dispersion according to any of Embodiments ASD1 to ASD12, consisting of cabozantinib and one or more anionic polymers. Embodiment ASD18 is an amorphous solid dispersion according to any of Embodiments ASD1 to ASD12, consisting essentially of cabozantinib and one or more anionic polymers.

Embodiment ASD19 is an amorphous solid dispersion according to any of Embodiments ASD1 to ASD18, wherein the one or more polymers includes an anionic polymer selected from the group consisting of polyvinyl acetate phthalate, hydroxypropyl methylcellulose acetate succinate, hydroxypropyl methylcellulose phthalate, methacrylic acid/ethyl acrylate copolymer, and combinations thereof. Embodiment ASD20 is an amorphous solid dispersion according to any of Embodiments ASD1 to ASD18, wherein the one or more polymers are each selected from the group consisting of polyvinyl acetate phthalate, hydroxypropyl methylcellulose acetate succinate, hydroxypropyl methylcellulose phthalate, methacrylic acid/ethyl acrylate copolymer, and combinations thereof.

Embodiment ASD21 is an amorphous solid dispersion according to any of Embodiments ASD1 to ASD20, wherein the one or more polymers exhibits pH-dependent solubility. Embodiment ASD22 is an amorphous solid dispersion according to any of Embodiments ASD1 to ASD20, consisting of cabozantinib and one or more polymers that exhibits pH-dependent solubility. Embodiment ASD23 is an amorphous solid dispersion according to any of Embodiments ASD1 to ASD20, consisting essentially of cabozantinib and one or more polymers that exhibits pH-dependent solubility.

Embodiment ASD24 is an amorphous solid dispersion according to any of Embodiments ASD1 to ASD23, comprising cabozantinib and one or more anionic polymers that exhibit pH-dependent solubility. Embodiment ASD25 is an amorphous solid dispersion according to any of Embodiments ASD1 to ASD23, consisting of cabozantinib and one or more anionic polymers that exhibit pH-dependent solubility. Embodiment ASD26 is an amorphous solid dispersion according to any of Embodiments ASD1 to ASD23, consisting essentially of cabozantinib and one or more anionic polymers that exhibit pH-dependent solubility.

Embodiment ASD27 is an amorphous solid dispersion according to any of Embodiments ASD1 to ASD26, comprising cabozantinib and one or more ionizable cellulose esters. Embodiment ASD28 is an amorphous solid dispersion according to any of Embodiments ASD1 to ASD26, consisting of cabozantinib and one or more ionizable cellulose esters. Embodiment ASD29 is an amorphous solid dispersion according to any of Embodiments ASD1 to ASD26, consisting essentially of cabozantinib and one or more ionizable cellulose esters. Embodiment ASD30 is an amorphous solid dispersion according to any of Embodiments ASD1 to ASD26, wherein the ionizable cellulose ester is selected from hydroxypropyl methylcellulose phthalate (HPMC-P) and hydroxypropyl methylcellulose acetate succinate (HPMC-AS).

Embodiment ASD31 is an amorphous solid dispersion according to any of Embodiments ASD1 to ASD30, wherein the one or more polymers comprises HPMC-P. Embodiment ASD32 is an amorphous solid dispersion according to any of Embodiments ASD1 to ASD30, wherein the amorphous solid dispersion comprises cabozantinib and HPMC-P. Embodiment ASD33 is an amorphous solid dispersion according to any of Embodiments ASD1 to ASD30, wherein the amorphous solid dispersion consists essentially of cabozantinib and HPMC-P. Embodiment ASD34 is an amorphous solid dispersion according to any of Embodiments ASD1 to ASD30, wherein the amorphous solid dispersion consists of cabozantinib and HPMC-P.

Embodiment ASD35 is an amorphous solid dispersion according to any of Embodiments ASD1 to ASD30, wherein the one or more polymers comprises HPMC-AS. Embodiment ASD36 is an amorphous solid dispersion according to any of Embodiments ASD1 to ASD30, wherein the amorphous solid dispersion comprises cabozantinib and HPMC-AS. Embodiment ASD37 is an amorphous solid dispersion according to any of Embodiments ASD1 to ASD30, wherein the amorphous solid dispersion consists essentially of cabozantinib and HPMC-AS. Embodiment ASD38 is an amorphous solid dispersion according to any of Embodiments ASD1 to ASD30, wherein the amorphous solid dispersion consists of cabozantinib and HPMC-AS.

Embodiment ASD39 is an amorphous solid dispersion according to any of Embodiments ASD1 to ASD26, wherein the one or more polymers comprises polyvinyl acetate phthalate (PVA-P). Embodiment ASD40 is an amorphous solid dispersion according to any of Embodiments ASD1 to ASD26, wherein the amorphous solid dispersion comprises cabozantinib and PVA-P. Embodiment ASD41 is an amorphous solid dispersion according to any of Embodiments ASD1 to ASD26, wherein the amorphous solid dispersion consists essentially of cabozantinib and PVA-P. Embodiment ASD42 is an amorphous solid dispersion according to any of Embodiments ASD1 to ASD26, wherein the amorphous solid dispersion consists of cabozantinib and PVA-P.

Embodiment ASD43 is the amorphous solid dispersion according to any of Embodiments ASD1 to ASD26, wherein the one or more polymers comprises a methacrylic acid/ethyl acrylate copolymer. Embodiment ASD44 is an amorphous solid dispersion according to any of Embodiments ASD1 to ASD26, wherein the amorphous solid dispersion comprises cabozantinib and a methacrylic acid/ethyl acrylate copolymer. Embodiment ASD45 is an amorphous solid dispersion according to any of Embodiments ASD1 to ASD26, wherein the amorphous solid dispersion consists essentially of cabozantinib and a methacrylic acid/ethyl acrylate copolymer. Embodiment ASD46 is an amorphous solid dispersion according to any of Embodiments ASD1 to ASD26, wherein the amorphous solid dispersion consists of cabozantinib and a methacrylic acid/ethyl acrylate copolymer. Embodiment ASD47 is the amorphous solid dispersion according to any of Embodiments ASD43 to ASD46, wherein the methacrylic acid/ethyl acrylate copolymer is insoluble in an aqueous medium at pH of 5 or lower, and soluble in an aqueous medium at pH 5.5 or greater.

Embodiment ASD48 is the amorphous solid dispersion according to any of Embodiments ASD1 to ASD12, wherein the one or more polymers comprises a hydroxypropyl methylcellulose. Embodiment ASD49 is the amorphous solid dispersion according to any of Embodiments ASD1 to ASD12, wherein the amorphous solid dispersion comprises cabozantinib and hydroxypropyl methylcellulose. Embodiment ASD50 is the amorphous solid dispersion according to any of Embodiments ASD1 to ASD12, wherein the amorphous solid dispersion consists essentially of cabozantinib and hydroxypropyl methylcellulose. Embodiment ASD51 is the amorphous solid dispersion according to any of Embodiments ASD1 to ASD12, wherein the amorphous solid dispersion consists of cabozantinib and hydroxypropyl methylcellulose. Embodiment ASD52 is the amorphous solid dispersion according to any of Embodiments ASD48 to ASD51, wherein the hydroxypropyl methylcellulose is a low molecular-weight hydroxypropyl methylcellulose characterized by a solution viscosity of 4.0-6.0 mPa·s.

Embodiment ASD53 is the amorphous solid dispersion according to any of Embodiments ASD1 to ASD12, wherein the one or more polymers comprises a vinylpyrrolidone/vinyl acetate copolymer. Embodiment ASD54 is the amorphous solid dispersion according to any of Embodiments ASD1 to ASD12, wherein the amorphous solid dispersion comprises cabozantinib and a vinylpyrrolidone/vinyl acetate copolymer. Embodiment ASD55 is the amorphous solid dispersion according to any of Embodiments ASD1 to ASD12, wherein the amorphous solid dispersion consists essentially of cabozantinib and a vinylpyrrolidone/vinyl acetate copolymer. Embodiment ASD56 is the amorphous solid dispersion according to any of Embodiments ASD1 to ASD12, wherein the amorphous solid dispersion consists of cabozantinib and a vinylpyrrolidone/vinyl acetate copolymer.

Embodiment ASD57 is the amorphous solid dispersion according to any of Embodiments ASD1 to ASD56, wherein the amorphous solid dispersion is prepared by a process comprising electrospraying. Embodiment ASD58 is the amorphous solid dispersion according to any of Embodiments ASD1 to ASD56, wherein the amorphous solid dispersion is an electrosprayed amorphous solid dispersion. Embodiment ASD59 is the amorphous solid dispersion according to any of Embodiments ASD1 to ASD56, wherein the amorphous solid dispersion is prepared by a process comprising spray drying. Embodiment ASD60 is the amorphous solid dispersion according to any of Embodiments ASD1 to ASD56, wherein the amorphous solid dispersion is a spray-dried amorphous solid dispersion.

Embodiment ASD61 is the amorphous solid dispersion according to any of Embodiments ASD1 to ASD60, wherein, when tested promptly after preparation, the amorphous solid dispersion is amorphous or essentially amorphous as determined by powder X-ray diffraction (PXRD).

Embodiment ASD62 is the amorphous solid dispersion according to any of Embodiments ASD1 to ASD61, wherein, when tested promptly after preparation, the amorphous solid dispersion exhibits a glass transition greater than 50° C. as determined by differential scanning calorimetry (DSC).

Embodiment ASD63 is the amorphous solid dispersion according to any of Embodiments ASD1 to ASD62, wherein the amorphous solid dispersion remains amorphous or essentially amorphous as determined by powder X-ray diffraction (PXRD) after storage at 40° C./protected for 3 months.

Embodiment ASD64 is the amorphous solid dispersion according to any of Embodiments ASD1 to ASD63, wherein the amorphous solid dispersion is characterized by an assay level of at least 95% as measured by high performance liquid chromatography (HPLC) after storage at 40° C./protected for 3 months. Embodiment ASD65 is the amorphous solid dispersion according to any of Embodiments ASD1 to ASD64, wherein the assay level of the amorphous solid dispersion is at least 97% after storage at 40° C./protected for 3 months. Embodiment ASD66 is the amorphous solid dispersion according to any of Embodiments ASD1 to ASD65, wherein the assay level of the amorphous solid dispersion is at least 99% after storage at 40° C./protected for 3 months.

Embodiment ASD67 is the amorphous solid dispersion according to any of Embodiments ASD1 to ASD66, wherein a glass transition temperature of the amorphous solid dispersion, as determined by differential scanning calorimetry (DSC), does not change by more than 10° C. after storage at 40° C./protected for 3 months. Embodiment ASD68 is the amorphous solid dispersion according to any of Embodiments ASD1 to ASD66, wherein a glass transition temperature of the amorphous solid dispersion, as determined by differential scanning calorimetry (DSC), does not change by more than 5° C. after storage at 40° C./protected for 3 months. Embodiment ASD69 is the amorphous solid dispersion according to any of Embodiments ASD1 to ASD66, wherein a glass transition temperature of the amorphous solid dispersion, as determined by differential scanning calorimetry (DSC), does not change by more than 3° C. after storage at 40° C./protected for 3 months.

Embodiment ASD70 is the amorphous solid dispersion according to any of Embodiments ASD1 to ASD69, wherein the amorphous solid dispersion comprises a total related substances as measured by HPLC of less than 2% after storage at 40° C./protected for 3 months. Embodiment ASD71 is the amorphous solid dispersion according to any of Embodiments ASD1 to ASD69, wherein the amorphous solid dispersion comprises a total related substances as measured by HPLC of less than 1% after storage at 40° C./protected for 3 months.

Embodiment PC1 is a pharmaceutical composition comprising the amorphous solid dispersion according to any of Embodiments ASD1 to ASD71. Embodiment PC2 is a pharmaceutical composition comprising the amorphous solid dispersion according to any of Embodiments ASD1 to ASD71, and one or more pharmaceutically acceptable additives. Embodiment PC3 is the pharmaceutical composition of Embodiment PC2, wherein the one or more pharmaceutically acceptable additives comprises one or more solubilizers, one or more buffering agent, one or more pH-adjusting agents, one or more surfactants, one or more antioxidants, one or more carriers, or a combination thereof. Embodiment PC4 is the pharmaceutical composition of Embodiment PC2, wherein the one or more pharmaceutically acceptable additives comprises one or more fillers, one or more binders, one or more lubricants, one or more disintegrants, one or more glidants, or a combination thereof. Embodiment PC5 is the pharmaceutical composition of Embodiment PC4, wherein the pharmaceutical composition is a solid dosage form suitable for oral administration.

Embodiment MT1 is a method of treating a proliferative disorder in a patient in need thereof, the method comprising administering to the patient a pharmaceutical composition according to any of Embodiments PC1 to PC5. Embodiment MT2 is a method of treating a proliferative disorder in a patient in need thereof, the method comprising administering to the patient a therapeutically effective amount of a pharmaceutical composition according to any of Embodiments PC1 to PC5.

Embodiment MT3 is a method according to Embodiment MT1 or MT2, wherein the proliferative disorder is renal cell carcinoma. Embodiment MT4 is a method according to Embodiment MT1 or MT2, wherein the proliferative disorder is hepatocellular carcinoma. Embodiment MT5 is a method according to Embodiment MT1 or MT2, wherein the proliferative disorder is differentiated thyroid cancer. Embodiment MT6 is a method according to any of Embodiments MT3 to MT5, wherein the therapeutically effective amount is 60 mg per day. Embodiment MT7 is a method according to any of Embodiments MT3 to MT5, wherein the therapeutically effective amount is 40 mg per day.

Embodiment MT8 is a method according to Embodiment MT1 or MT2, wherein the proliferative disorder is medullary thyroid cancer. Embodiment MT9 is a method according to Embodiment MT8, wherein the 140 mg per day.

The present disclosure will be further illustrated and/or demonstrated in the following Examples, which are given for illustration/demonstration purposes only and are not intended to limit the disclosure in any way.

EXAMPLES

Example 1. Preparation and Characterization of Cabozantinib ASDs with Various Polymers Cabozantinib ASDs were prepared using a variety of polymers, and selected characterization tests were run on the ASDs. ASDs comprising cabozantinib free base and a polymeric stabilizer were prepared, using the polymers specified in Table 1. For this study, the drug:polymer ratio (w/w) was fixed at 50:50 for all polymers except polyethylene glycol (PEG 8000), which was 80:20.

TABLE 1

Summary of ASD compositions for the ASDs of Example 1.

| ASD | Identifier | Polymer |
|---|---|---|
| Cabozantinib 50:50 PVP/VA | 0091-08-01 | vinylpyrrolidone/vinyl acetate copolymer (KOLLIDON VA 64; BASF) |
| Cabozantinib 50:50 HPMC | 0091-09-01 | hydroxypropyl methylcellulose (Hypromellose E5; Dow) |
| Cabozantinib 50:50 HPC | 0091-10-01 | hydroxypropyl cellulose (HPC-L; Nisso) |
| Cabozantinib 50:50 SOLUPLUS | 0091-13-01 | polyvinyl caprolactam-polyvinyl acetate-polyethylene glycol graft copolymer (SOLUPLUS; BASF) |
| Cabozantinib 50:50 PVA-P | 0091-14-01 | polyvinyl acetate phthalate (PHTHALAVIN; Colorcon) |
| Cabozantinib 50:50 HPMC-AS | 0091-15-01 | hydroxypropyl methylcellulose acetate succinate (AQOAT AS-MG; Shin-Etsu) |
| Cabozantinib 50:50 HPMC-P | 0091-17-01 | hydroxypropyl methylcellulose phthalate (HPMC-P HP-50; Shin-Etsu) |
| Cabozantinib 50:50 L100-55 | 0091-18-01 | methacrylic acid/ethyl acrylate copolymer (EUDRAGIT L100-55; Evonik) |
| Cabozantinib 50:50 E100 | 0091-19-01 | dimethylaminoethyl methacrylate/butyl methacrylate/methyl methacrylate copolymer (EUDRAGIT E100; Evonik) |
| Cabozantinib 80:20 PEG 8000 | 0091-29-01 | Polyethylene glycol (PEG 8000; Sigma-Aldrich) |

To prepare the ASDs (except the PEG 8000 ASD), appropriate quantities of cabozantinib free base and polymer were dissolved in a solvent system to provide a liquid feedstock having a total solids concentration of about 30 mg/mL. The solvent system was a 50:50 (v/v) mixture of methanol and dichloromethane.

The ASDs were formed by spray drying the liquid feedstock using a Buchi B-290 spray dryer equipped with a two-fluid nozzle and a Buchi B-295 inert loop. For each spray run, the spray process parameters, such as inlet temperature, pump rate, outlet temperature, etc. were adjusted to achieve an acceptable outcome. For all ASDs (except the PEG 8000 ASD), inlet temperature was set at 85-95° C., pump rate was set at 20%, and outlet temperature was 50-60° C. In each case, the resulting ASD powder was collected using a cyclone separator. After spray drying, each ASD powder was dried at 35-45° C. under vacuum for at least 18 hours to remove residual solvents.

The PEG 8000 ASD was prepared similarly, except the solvent system was an approximately 52:48 (v/v) mixture of methanol and dichloromethane, and the total solids content was about 20 mg/mL. The inlet temperature was set at 50-60° C., pump rate was set at 20%, and outlet temperature was 30-35° C.

The ASD powders were also evaluated after preparation for amorphicity (PXRD), water content (Karl Fisher), glass transition temperature (DSC), and total related substances (HPLC) using suitable analytical methods. Each of the ASD powders was amorphous as determined by PXRD. Results for the other evaluations are summarized in Table 2, along with results for the cabozantinib free base starting material. Experimental details for each evaluation are provided below.

TABLE 2

Summary of data for observed glass transition temperature ($T_g$), water content, and total related substances for the ASDs of Example 1.

| ASD | Identifier | Glass Transition (° C.) | Water Content (% water) | Total Related Substances (% Area) |
|---|---|---|---|---|
| Cabozantinib (free base) | 1924802 | Not analyzed | 0.75 | 0.44 |
| Cabozantinib 50:50 PVP/VA | 0091-08-01 | 96.30 | 2.21 | 0.51 |
| Cabozantinib 50:50 HPMC | 0091-09-01 | 100.04 | 1.81 | 0.52 |
| Cabozantinib 50:50 HPC | 0091-10-01 | 56.52 | 1.48 | 0.53 |
| Cabozantinib 50:50 SOLUPLUS | 0091-13-01 | 72.62 | 1.37 | 0.53 |
| Cabozantinib 50:50 PVA-P | 0091-14-01 | 132.18 | 1.95 | 0.53 |
| Cabozantinib 50:50 HPMC-AS | 0091-15-01 | 98.75 | 1.17 | 0.55 |
| Cabozantinib 50:50 HPMC-P | 0091-17-01 | 113.79 | 1.64 | 0.54 |

TABLE 2-continued

Summary of data for observed glass transition temperature ($T_g$), water content, and total related substances for the ASDs of Example 1.

| ASD | Identifier | Glass Transition (° C.) | Water Content (% water) | Total Related Substances (% Area) |
|---|---|---|---|---|
| Cabozantinib 50:50 L100-55 | 0091-18-01 | 122.50 | 1.80 | 0.53 |
| Cabozantinib 50:50 E100 | 0091-19-01 | 65.01, 128.46* | 1.01 | 0.55 |
| Cabozantinib 80:20 PEG 8000 | 0091-29-01 | 32.35 | 1.55 | 0.73 |

*The two glass transitions likely represent separate transitions for polymer and for cabozantinib.

Amorphicity

For each ASD, amorphicity (i.e., the lack of crystallinity) was assessed by PXRD promptly after preparation (i.e., within a few days after preparation, and stored under protected conditions at ambient temperature and humidity after preparation and before testing). Diffraction patterns were obtained using a Rigaku MiniFlex 600. The X-ray source was a long anode Cu Kα. Samples were prepared by placing a small amount of ASD powder on a Rigaku zero-background sample holder with a 0.1 mm indent. A glass slide was then used to firmly pack the powder and ensure the surface of the sample was level with the edge of the sample holder. Instrument details and measurement conditions are specified in Table 3.

TABLE 3

Rigaku MiniFlex instrument parameters for PXRD analysis.

| Parameter | Setting |
|---|---|
| Soller Slits | 5.0 deg |
| Spin | On |
| Voltage | 40 kV |
| Current | 15 mA |
| Scan axis | Theta/2Theta Continuous |
| Start | 5.0° 2θ |
| Stop | 40.0° 2θ |
| Step | 0.02° 2θ |
| Speed | 5.0°/min |

Water Content

Water content was determined by Karl Fischer coulometric titration method, using a Mettler Toledo C30S Karl Fischer with Stromboli Oven Sampler. Approximately 40-50 mg of ASD powder was weighed into a glass Stromboli sample vial and the vial was immediately sealed with a foil coated vial cover, and a rubber vial cap cover was placed on top of the sample vial. The vial was then placed onto instrument and analysis was conducted using nitrogen carrier gas. Instrument details and measurement conditions are specified in Table 4.

TABLE 4

Karl Fisher instrument and measurement conditions.

| Parameter | Condition |
|---|---|
| Drift duration | 3 min |
| Drift wait time | 60 sec |
| Maximum drift allowance | 25 μg/min |
| Oven temperature | 130° C. |
| Mix time | 60 sec |
| Stir speed | 50% |

Glass Transition Temperature

Modulated differential scanning calorimetry (mDSC) analysis was run on a TA Instruments Model Q200, equipped with a RCS90 refrigerated cooling system, to assess glass transition temperatures (Tg) of the ASDs. In general, about 5-10 mg of ASD powder was loaded in a TA $T_{zero}$ low-mass aluminum pan and sealed with a $T_{zero}$ lid. Instrument details and measurement conditions are provided in Table 5.

TABLE 5

TA Q200 mDSC instrument and measurement conditions.

| Parameter | Setting |
|---|---|
| Equilibration | 0° C. for 5 min |
| Modulation | ±0.48° C. every 60 s |
| Ramp | 3.00° C./min |
| Final Temperature | 200° C. |

Total Related Substances

Total related substances was determined by HPLC using a Waters Acquity H-Class UPLC instrument utilizing a Waters Acquity BEH C18, 2.1×50 mm, 1.7 μm column. The instrument and measurement conditions are specified in Table 6, while the gradient profile is listed in Table 7. Sample solutions of each ASD were prepared by accurately weighing ASD powder into a volumetric flask, and diluted in 1:1:1 methanol:ethanol:water. The final concentration of the analyte (cabozantinib) in the sample was approximately 0.2 mg/ml.

TABLE 6

HPLC instrument and measurement conditions.

| Parameter | Condition |
|---|---|
| Mobile Phase A | 0.1% TFA in water |
| Mobile Phase B | 0.085% TFA in acetonitrile |
| Flow | 0.8 ml/min |
| Injection volume | 1 μL |
| Column temperature | 45° C. |
| Detector Wavelength | 249 nm |
| Run-time | 4 min |

TFA = trifluoroacetic acid

TABLE 7

HPLC instrument gradient profile.

| Time (min) | % Mobile Phase A | % Mobile Phase B |
|---|---|---|
| 0 | 90 | 10 |
| 3.00 | 0 | 100 |
| 3.01 | 90 | 10 |
| 4.00 | 90 | 10 |

Individual related substances were calculated as peak area percent. Total related substances is calculated as the sum of all detected individual related substances.

Example 2. Stability of Cabozantinib ASDs Under Accelerated Conditions

Several of the ASDs prepared according to Example 1 were placed on stability under accelerated conditions at 40° C./protected, and separately at 40° C./75% RH. The ASDs were assessed at t=0, 1 month, 2 months, and 3 months for amorphicity (PXRD), glass transition temperature (DSC), and assay/related substances (HPLC) using suitable analytical methods (as described in Example 1).

Amorphicity

Amorphicity (i.e., the lack of crystallinity) for the ASDs was assessed by PXRD. Results are provided in Table 8 for samples held at 40° C./protected. Samples were deemed "Amorphous" if no crystalline character was detected, and "Crystalline" if characteristic peaks indicating crystalline material were observed.

TABLE 8

Summary of amorphicity data (PXRD) for Example 2, for ASD samples held at 40° C./protected.

| ASD | Identifier | Amorphous/Crystalline t = 0 | 1 month | 2 months | 3 months |
|---|---|---|---|---|---|
| Cabozantinib 50:50 PVP/VA | 0091-08-01 | Amorphous | Amorphous | Amorphous | Amorphous |
| Cabozantinib 50:50 HPMC | 0091-09-01 | Amorphous | Amorphous | Amorphous | Amorphous |
| Cabozantinib 50:50 HPC | 0091-10-01 | Amorphous | Amorphous | Amorphous | Amorphous |
| Cabozantinib 50:50 SOLUPLUS | 0091-13-01 | Amorphous | Amorphous | Amorphous | Amorphous |
| Cabozantinib 50:50 PVA-P | 0091-14-01 | Amorphous | Amorphous | Amorphous | Amorphous |
| Cabozantinib 50:50 HPMC-AS | 0091-15-01 | Amorphous | Amorphous | Amorphous | Amorphous |
| Cabozantinib 50:50 HPMC-P | 0091-17-01 | Amorphous | Amorphous | Amorphous | Amorphous |
| Cabozantinib 50:50 L100-55 | 0091-18-01 | Amorphous | Amorphous | Amorphous | Amorphous |
| Cabozantinib 50:50 E100 | 0091-19-01 | Amorphous | Amorphous | Amorphous | Amorphous |
| Cabozantinib 80:20 PEG 8000 | 0091-29-01 | Amorphous | Crystalline | Not analyzed | Not analyzed |

As shown in Table 8, each ASD was amorphous after preparation. Except for the Cabozantinib:PEG 8000 ASD, the ASDs continued to show amorphous character after 3 months. Similar results were obtained for the samples held at 40° C./75% RH.

The Cabozantinib 80:20 PEG 8000 ASD was amorphous at t=0, but showed peaks characteristic of crystalline material within 1 month under storage at 40° C./protected. Because crystallinity was observed after a short period of time for the Cabozantinib 80:20 PEG 800 ASDs under these storage conditions, this result was considered disqualifying, and this ASD would not be considered suitable for use in a pharmaceutical composition.

Glass Transition Temperature

Glass transition characteristics were measured using a suitable DSC method as described in Example 1. Results are provided in Table 9 for samples held at 40° C./protected.

TABLE 9

Summary of glass transition (DSC) data for Example 2, for ASD samples held at 40° C./protected.

| ASD | Identifier | Glass Transition ($T_g$) Temperature (° C.) t = 0 | 1 month | 2 month | 3 months |
|---|---|---|---|---|---|
| Cabozantinib 50:50 PVP/VA | 0091-08-01 | 96.30 | 102.47 | 102.95 | 104.74 |
| Cabozantinib 50:50 HPMC | 0091-09-01 | 100.04 | 101.08 | 101.11 | 102.20 |

TABLE 9-continued

Summary of glass transition (DSC) data for Example 2, for ASD samples held at 40° C./protected.

| ASD | Identifier | Glass Transition ($T_g$) Temperature (° C.) t = 0 | 1 month | 2 month | 3 months |
|---|---|---|---|---|---|
| Cabozantinib 50:50 HPC | 0091-10-01 | 56.52 | 52.23 | 67.96** | 75.00** |
| Cabozantinib 50:50 SOLUPLUS | 0091-13-01 | 72.62 | None Detected | None Detected | None Detected |
| Cabozantinib 50:50 PVA-P | 0091-14-01 | 132.18 | 131.38 | 131.63 | 130.09 |
| Cabozantinib 50:50 HPMC-AS | 0091-15-01 | 98.75 | 98.97 | 98.42 | 99.79 |
| Cabozantinib 50:50 HPMC-P | 0091-17-01 | 113.79 | 114.66 | 113.63 | 113.99 |
| Cabozantinib 50:50 L100-55 | 0091-18-01 | 122.50 | 123.26 | 122.61 | 123.41 |
| Cabozantinib 50:50 E100 | 0091-19-01 | 65.01, 128.46* | 63.73, 128.13* | 72.60 | 83.92** |
| Cabozantinib 80:20 PEG 8000 | 0091-29-01 | 32.35 | Not analyzed | Not analyzed | Not analyzed |

*The two glass transitions likely represent separate transitions for polymer and for cabozantinib.
**Broad transition, difficult to integrate.

Each of the ASDs exhibited a single glass transition at t=0, with the exception of Cabozantinib 50:50 E100, which exhibited two transitions. The two transitions likely represent separate transitions for the polymer and for cabozantinib, suggesting a possible phase separation. After storage for 1 month at 40° C./protected, two transitions were again observed for this ASD. Although this ASD did not exhibit crystalline character by PXRD, because of the separate transitions, it is thought that this ASD may not be as suitable as some others for providing properties desirable for a pharmaceutical composition.

The Cabozantinib 50:50 SOLUPLUS ASD exhibited a t=0 glass transition at approximately 72° C.; however, after storage for 1 month at 40° C./protected, no distinct transition was observed. The observed change in glass transition for this ASD suggested that some type of physical change may have occurred under accelerated conditions. Although this ASD did not exhibit crystalline character by PXRD, it is thought that this ASD may not be as suitable as some others for providing properties desirable for a pharmaceutical composition.

The Cabozantinib 80:20 PEG 8000 exhibited a t=0 glass transition at approximately 32° C. This was deemed too low of a glass transition temperature to provide the desired physical stability. This ASD will not be further assessed, and is considered not suitable for a pharmaceutical application.

Cabozantinib 50:50 PVP/VA exhibited a glass transition temperature that increased by about 6-9° C. after storage over a period of months, but continued to exhibit a single transition. Similar results were obtained for a sample held at 40° C./75% RH for three months.

Cabozantinib 50:50 HPC exhibited a glass transition temperature that increased significantly after storage over a period of months, and exhibited a broad transition. The observed change in glass transition for this ASD suggested that some type of physical change may have occurred under accelerated conditions. Although this ASD did not exhibit crystalline character by PXRD, it is thought that this ASD may not be as suitable as some others for providing properties desirable for a pharmaceutical composition.

The following ASDs exhibited a very stable glass transition temperature (changing by not more than about 2° C.) after storage over 3 months: Cabozantinib 50:50 HPMC; Cabozantinib 50:50 PVA-P; Cabozantinib 50:50 HPMC-AS; Cabozantinib 50:50 HPMC-P; Cabozantinib 50:50 L100-55. Similar results were obtained for these ASDs for samples held at 40° C./75% RH for three months.

Assay/Related Substances

Assay values and total related substances were determined for the ASDs after preparation (t=0) and at the designated stability timepoints using an appropriate HPLC method (as described in Example 1). Measured assay values for the ASDs for samples held at 40° C./protected are listed in Table 10. The reported assay values have been corrected for water content (determined by Karl Fischer coulometric titration method). Measured total related substances values for the ASDs are listed in Table 11. For reference, cabozantinib free base was stored and tested using the same methods; results are reported in Tables 10 and 11.

TABLE 10

Summary of assay (HPLC) data (corrected for water content) for Example 2, for ASD samples held at 40° C./protected.

| ASD | Identifier | Assay (%) t = 0 | 1 month | 2 months | 3 months |
|---|---|---|---|---|---|
| Cabozantinib (free base) | 1924802 | 99.2 | 99.9 | 99.6 | 99.0 |
| Cabozantinib 50:50 PVP/VA | 0091-08-01 | 101.9 | 101.9 | 101.8 | 100.5 |

TABLE 10-continued

Summary of assay (HPLC) data (corrected for water content) for Example 2, for ASD samples held at 40° C./protected.

| ASD | Identifier | Assay (%) t = 0 | 1 month | 2 months | 3 months |
|---|---|---|---|---|---|
| Cabozantinib 50:50 HPMC | 0091-09-01 | 101.5 | 101.1 | 100.9 | 103.0 |
| Cabozantinib 50:50 HPC | 0091-10-01 | 100.8 | 100.7 | 99.4 | 97.0 |
| Cabozantinib 50:50 SOLUPLUS | 0091-13-01 | 102.0 | 101.0 | 99.4 | 97.6 |
| Cabozantinib 50:50 PVA-P | 0091-14-01 | 101.0 | 97.3 | 98.6 | 100.1 |
| Cabozantinib 50:50 HPMC-AS | 0091-15-01 | 101.1 | 100.3 | 100.4 | 100.0 |
| Cabozantinib 50:50 HPMC-P | 0091-17-01 | 101.1 | 101.9 | 101.1 | 100.5 |
| Cabozantinib 50:50 L100-55 | 0091-18-01 | 102.9 | 103.2 | 101.9 | 102.1 |
| Cabozantinib 50:50 E100 | 0091-19-01 | 100.4 | 93.1 | 88.7 | 84.4 |
| Cabozantinib 80:20 PEG 8000 | 0091-29-01 | 100.0 | Not analyzed | Not analyzed | Not analyzed |

TABLE 11

Summary of total related substances (HPLC) data for Example 2, for ASD samples held at 40° C./protected.

| ASD | Identifier | Total Related Substances (%) t = 0 | 1 month | 2 months | 3 months |
|---|---|---|---|---|---|
| Cabozantinib (free base) | 1924802 | 0.44 | 0.52 | 0.44 | 0.38 |
| Cabozantinib 50:50 PVP/VA | 0091-08-01 | 0.51 | 0.70 | 0.86 | 1.13 |
| Cabozantinib 50:50 HPMC | 0091-09-01 | 0.52 | 0.92 | 1.20 | 1.56 |
| Cabozantinib 50:50 HPC | 0091-10-01 | 0.53 | 1.79 | 2.32 | 3.76 |
| Cabozantinib 50:50 SOLUPLUS | 0091-13-01 | 0.53 | 1.59 | 2.34 | 3.57 |
| Cabozantinib 50:50 PVA-P | 0091-14-01 | 0.53 | 0.68 | 0.72 | 0.58 |
| Cabozantinib 50:50 HPMC-AS | 0091-15-01 | 0.55 | 0.87 | 0.96 | 1.21 |
| Cabozantinib 50:50 HPMC-P | 0091-17-01 | 0.54 | 0.82 | 1.10 | 1.10 |
| Cabozantinib 50:50 L100-55 | 0091-18-01 | 0.53 | 0.62 | 0.62 | 0.58 |
| Cabozantinib 50:50 E100 | 0091-19-01 | 0.55 | 2.82 | 5.06 | 7.61 |
| Cabozantinib 80:20 PEG 8000 | 0091-29-01 | 0.73 | Not analyzed | Not analyzed | Not analyzed |

As seen in Tables 10 and 11, the Cabozantinib 50:50 E100 ASD exhibited a significant drop in the measured assay value over 1 month storage, and a significant increase in total related substances was observed. Similar changes were noted between the 1-month and 2-month results, and between the 2-month and 3-month results. It is thought that this ASD is unlikely to provide the required chemical stability required for an improved pharmaceutical composition. Similar trends were observed at a lesser degree for the Cabozantinib 50:50 HPC ASD and Cabozantinib 50:50 SOLUPLUS ASD. Similar results were also obtained for these ASDs for samples held at 40° C./75% RH for three months.

As demonstrated by the results reported in Tables 10 and 11, the remaining ASDs exhibited suitably high assay values (exceeding 97% in all cases) and suitably low related substances values (less than 2% in all cases at 1 month, and less than 2.5% after 2 months) that did not change unexpectedly over time, indicating that the ASDs were chemically stable under the accelerated storage conditions. Similar results were also obtained for these ASDs for samples held at 40° C./75% RH for three months, with suitably high assay values (exceeding 97% in all cases) and suitably low related substances values (less than 3% in all cases after 3 months).

Taken together, the results of the above experiments indicate that the following polymers may provide particularly desirable physical and chemical stability for an ASD suitable for pharmaceutical applications: PVP/VA; HPMC; PVA-P; HPMC-AS; HPMC-P; methacrylic acid/ethyl acrylate copolymer (e.g., EUDRAGIT L100-55).

The results further indicate that the following polymers may be particularly promising for providing the desired physical and chemical stability for an ASD suitable for pharmaceutical applications: PVA-P; HPMC-AS; HPMC-P; methacrylic acid/ethyl acrylate copolymer (e.g., EUDRAGIT L100-55). Each of these is an ionizable polymer, particularly an anionic polymer. Therefore, ionizable polymers may be particularly suitable for ASDs comprising cabozantinib in the practice of the disclosure. More specifically, anionic polymers may be particularly suitable for ASDs comprising cabozantinib in the practice of the disclosure.

Example 3. Canine In Vivo Pharmacokinetic Study

An in vivo study was performed on canine subjects to investigate the pharmacokinetics observed upon administration of cabozantinib ASDs.

The pharmacokinetics of five test compositions (commercially obtained CABOMETYX as a reference composition, and four cabozantinib ASD compositions) was evaluated by peroral administration in fasted male beagle dogs. A summary of the study design is provided in Table 12. The study included ASDs of cabozantinib with three different polymers (HPMC-P, EUDRAGIT L100-55, PVA-P) prepared by conventional spray drying, and one ASD of cabozantinib with HPMC-P prepared by electrospraying. All ASDs were prepared at a drug:polymer ratio of 50:50.

To prepare the spray-dried ASDs, appropriate quantities of cabozantinib free base and polymer were dissolved in a solvent system to provide a liquid feedstock having a total solids concentration of about 30 mg/mL. The solvent system was a 50:50 (v/v) mixture of methanol and dichloromethane. The spray-dried ASDs were formed by spray drying the liquid feedstock using a Buchi B-290 spray dryer equipped with a two-fluid nozzle and a Buchi B-295 inert loop. For each spray run, the spray process parameters, such as inlet temperature, pump rate, outlet temperature, etc. were adjusted to achieve an acceptable outcome. For all ASDs, inlet temperature was set at 85-95° C., pump rate was set at 20%, and outlet temperature was 55-65° C. In each case, the resulting ASD powder was collected using a cyclone separator. After spray drying, each ASD powder was dried at 35-45° C. under vacuum for at least 17 hours to remove residual solvents.

To prepare the electrosprayed ASD, appropriate quantities of cabozantinib free base and HPMC-P were dissolved in a solvent system to provide a liquid feedstock having a total solids concentration of about 20 mg/mL. The solvent system was a 50:50 (v/v) mixture of methanol and methyl ethyl ketone (MEK). The ASD was formed by electrospraying the liquid feedstock using the Nanocopoeia spray machine FLEX 20X. The FLEX 20X machine utilized 48 nozzles, which were arranged in a circular array consisting of 6 nozzles per array. Each nozzle had twenty-four tips (D24). Spray process parameters, such as extractor voltage and flow rate, were adjusted to achieve an acceptable spray plume. The following settings were utilized for the spray run: Nozzle height was set to 3.0 inches; Dryer tray voltage was 40 kV; Extractor voltage was set to 15.5 kV; Spray rate was set to 6.9-7.5 mL/min; Environmental Control Unit (ECU) setting was set to 57% target relative humidity (actual observed 45-47% RH).

For the in vivo canine study, cabozantinib ASD compositions were dosed as a suspension formulation. Each suspension was prepared (using the corresponding ASD powder) to provide nominal dosage of 10 mg/mL cabozantinib, in a buffered aqueous vehicle (0.5% methylcellulose in 0.5 mM citric acid buffer). Each dose was 6.0 mL of the suspension, providing a total of nominally 60 mg in each dose.

TABLE 12

Dosing details for study legs 1-5 for canine in vivo study of Example 3.

| Study Leg | Composition | How Dosed |
|---|---|---|
| 1 | CABOMETYX (60 mg tablet) | Intact tablet |
| 2 | ASD-A (Cabozantinib 50:50 HPMC-P; spray dried) | 6 mL of 10 mg/mL suspension |
| 3 | ASD-B (Cabozantinib 50:50 EUDRAGIT L100-55; spray dried) | 6 mL of 10 mg/mL suspension |
| 4 | ASD-C (Cabozantinib 50:50 PVA-P; spray dried) | 6 mL of 10 mg/mL suspension |
| 5 | ASD-D (Cabozantinib 50:50 HPMC-P; electrosprayed) | 6 mL of 10 mg/mL suspension |

Each study leg included ten dogs, weighing between 10 and 15 kg each. Dogs were housed one per cage. The study employed a crossover study design, with the same dogs receiving each dose, following a minimum one-week washout period between each leg of the study.

Each leg of the study was conducted as follows: Dogs were fasted for a minimum of twelve hours prior to dose administration. A pre-dosing blood sample was obtained. Immediately prior to dosing, each dog received a pretreatment of 25 mL pH 2.5 phosphate buffer solution via oral gavage tube. CABOMETYX was dosed (at time zero) perorally as an intact tablet. ASD suspensions were dosed (at time zero) perorally using a syringe. Post dosing, each dog received an additional 10 mL pH 2.5 phosphate buffer solution via oral gavage tube. Following dosing, blood samples were collected at 30 minutes, 1, 1.5, 2, 3, 4, 6, 8, 12, 18, 24, and 36 hours. Food was made available four hours post-dose. Dogs were supplied with water ad libitum throughout.

Some minor dosing-related reactions were observed. In Leg 1, one animal had ~50 g of food emesis at the 12 hour time point. In Leg 3, the same animal had ~50 g food emesis at the 8 hour time point. In Leg 4, the same animal had ~20 mL white foamy emesis immediately following dosing. (This event likely decreased the exposure observed for this canine, which slightly affected the pooled pharmacokinetic results for this study leg.) In Leg 2, four animals were inappetent at the 8 and 18 hour time points. These dosing-related reactions were not deemed significant to the relevant conclusions of the study.

Pharmacokinetics

Plasma concentrations of cabozantinib were determined using a qualified LC-MS/MS method. Pharmacokinetic analysis was conducted by a non-compartmental model using Phoenix WinNonlin v. 8.0 software.

Pharmacokinetic parameters were calculated from the time course of the plasma concentrations. All pre-dose samples were below the limit of quantitation (1 ng/mL). Independent of formulation, all post-dose time points exhibited concentrations of cabozantinib that were above the limit of quantitation. The maximum plasma concentration ($C_{max}$) and the time to reach maximum plasma drug concentration ($T_{max}$) after oral dosing were determined from the data.

Calculated pharmacokinetic parameters for the respective study legs are given in Tables 13 through 17. (Min and Max values are provided for only numeric values, i.e., not considering any values listed as "ND".) Table 18 summarizes the mean pharmacokinetic parameters across the study legs. The tables below include the following abbreviations and notations:

- $C_{max}$: maximum plasma concentration;
- $T_{max}$: time of maximum plasma concentration;
- $t_{1/2}$: half-life;
- $MRT_{last}$: mean residence time, calculated to the last observable time point;
- $AUC_{last}$: area under the curve, calculated to the last observable time point;
- $AUC_{0-inf}$: area under the curve, extrapolated to infinity;
- ND: not determined.

TABLE 13

Minimum, maximum, and mean (±SD) pharmacokinetic parameters for Leg 1 of the canine in vivo study of Example 3. Leg 1 - CABOMETYX 60 mg tablet

| Parameters | Min (n = 10) | Max (n = 10) | Mean | SD |
|---|---|---|---|---|
| Dose (mg/kg) | 4.17 | 5.50 | 4.78 | 0.53 |
| $C_{max}$ (ng/mL) | 558 | 1401 | 847 | 400 |
| $T_{max}$ (hr) | 1.00 | 4.00 | 1.83 | 1.04 |
| $t_{1/2}$ (hr) | 4.98 | 76.7 | 8.71 | 0.27 |
| $MRT_{last}$ (hr) | 6.56 | 15.2 | 7.96 | 0.73 |
| $AUC_{last}$ (hr · ng/mL) | 3237 | 12105 | 5256 | 1988 |
| $AUC_{0-inf}$ (hr · ng/mL) | 3360 | 12897 | 5445 | 2060 |
| | Dose-normalized values[a] | | | |
| $AUC_{last}$ (hr · kg · ng/mL/mg) | 631 | 2231 | 1112 | 424 |
| $AUC_{0-inf}$ (hr · kg · ng/mL/mg) | 655 | 2314 | 1152 | 439 |

[a]Dose-normalized by dividing the parameter by the nominal dose in mg/kg.

TABLE 14

Minimum, maximum, and mean (±SD) pharmacokinetic parameters for Leg 2 of the canine in vivo study of Example 3. Leg 2 - ASD-A (HPMC-P; spray dried)

| Parameters | Min (n = 10) | Max (n = 10) | Mean | SD |
|---|---|---|---|---|
| Dose (mg/kg) | 4.20 | 5.50 | 4.75 | 0.47 |
| $C_{max}$ (ng/mL) | 784 | 1994 | 1342 | 493 |
| $T_{max}$ (hr) | 1.00 | 3.00 | 1.17 | 0.29 |
| $t_{1/2}$ (hr) | 5.76 | 31.12 | 9.48 | 1.71 |
| $MRT_{last}$ (hr) | 5.65 | 14.55 | 7.36 | 0.41 |
| $AUC_{last}$ (hr · ng/mL) | 4310 | 22295 | 6570 | 2168 |
| $AUC_{0-inf}$ (hr · ng/mL) | 4426 | 38365 | 6916 | 2463 |
| | Dose-normalized values[a] | | | |
| $AUC_{last}$ (hr · kg · ng/mL/mg) | 855 | 4724 | 1398 | 473 |
| $AUC_{0-inf}$ (hr · kg · ng/mL/mg) | 878 | 8128 | 1469 | 523 |

[a]Dose-normalized by dividing the parameter by the nominal dose in mg/kg.

TABLE 15

Minimum, maximum, and mean (±SD) pharmacokinetic parameters for Leg 3 of the canine in vivo study of Example 3. Leg 3 - ASD-B (EUDRAGIT L100-55; spray dried)

| Parameters | Min (n = 10) | Max (n = 10) | Mean | SD |
|---|---|---|---|---|
| Dose (mg/kg) | 4.11 | 5.50 | 4.76 | 0.57 |
| $C_{max}$ (ng/mL) | 813 | 1641 | 999 | 20.1 |
| $T_{max}$ (hr) | 1.00 | 3.00 | 2.00 | 0.87 |

TABLE 15-continued

Minimum, maximum, and mean (±SD) pharmacokinetic parameters for Leg 3 of the canine in vivo study of Example 3. Leg 3 - ASD-B (EUDRAGIT L100-55; spray dried)

| Parameters | Min (n = 10) | Max (n = 10) | Mean | SD |
|---|---|---|---|---|
| $t_{1/2}$ (hr) | 5.03 | 13.4 | 10.4 | 0.21 |
| $MRT_{last}$ (hr) | 6.49 | 12.9 | 8.86 | 0.13 |
| $AUC_{last}$ (hr · ng/mL) | 6276 | 20130 | 7309 | 1209 |
| $AUC_{0-inf}$ (hr · ng/mL) | 6693 | 21565 | 7792 | 1222 |
| | Dose-normalized values[a] | | | |
| $AUC_{last}$ (hr · kg · ng/mL/mg) | 1356 | 4194 | 1537 | 186 |
| $AUC_{0-inf}$ (hr · kg · ng/mL/mg) | 1404 | 4493 | 1638 | 178 |

[a]Dose-normalized by dividing the parameter by the nominal dose in mg/kg.

TABLE 16

Minimum, maximum, and mean (±SD) pharmacokinetic parameters for Leg 4 of the canine in vivo study of Example 3. Leg 4 - ASD-C (PVA-P; spray dried)

| Parameters | Min (n = 10) | Max (n = 10) | Mean | SD |
|---|---|---|---|---|
| Dose (mg/kg) | 4.17 | 5.56 | 4.78 | 0.53 |
| $C_{max}$ (ng/mL) | 538 | 1800 | 1409 | 341 |
| $T_{max}$ (hr) | 1.00 | 3.00 | 1.67 | 0.58 |
| $t_{1/2}$ (hr) | 6.74 | 17.6 | 10.2 | 0.93 |
| $MRT_{last}$ (hr) | 5.89 | 15.3 | 8.34 | 0.93 |
| $AUC_{last}$ (hr · ng/mL) | 4494 | 15318 | 8632 | 2124 |
| $AUC_{0-inf}$ (hr · ng/mL) | 4797 | 19346 | 9163 | 2529 |
| | Dose-normalized values[a] | | | |
| $AUC_{last}$ (hr · kg · ng/mL/mg) | 808 | 3245 | 1809 | 388 |
| $AUC_{0-inf}$ (hr · kg · ng/mL/mg) | 863 | 4099 | 1918 | 458 |

[a]Dose-normalized by dividing the parameter by the nominal dose in mg/kg.

TABLE 17

Minimum, maximum, and mean (±SD) pharmacokinetic parameters for Leg 5 of the canine in vivo study of Example 3. Leg 5 - ASD-D (HPMC-P; electrosprayed)

| Parameters | Min (n = 10) | Max (n = 10) | Mean | SD |
|---|---|---|---|---|
| Dose (mg/kg) | 4.26 | 5.36 | 5.05 | 0.23 |
| $C_{max}$ (ng/mL) | 332 | 2398 | 1216 | 1063 |
| $T_{max}$ (hr) | 1.50 | 4.00 | 1.83 | 0.29 |
| $t_{1/2}$ (hr) | 5.16 | 22.4 | 8.00 | 0.71 |
| $MRT_{last}$ (hr) | 6.13 | 13.6 | 8.72 | 0.75 |
| $AUC_{last}$ (hr · ng/mL) | 2848 | 26984 | 7694 | 5266 |
| $AUC_{0-inf}$ (hr · ng/mL) | 2972 | 39159 | 8011 | 5520 |
| | Dose-normalized values[a] | | | |
| $AUC_{last}$ (hr · kg · ng/mL/mg) | 579 | 6246 | 1498 | 966 |
| $AUC_{0-inf}$ (hr · kg · ng/mL/mg) | 604 | 9064 | 1559 | 1012 |

[a]Dose-normalized by dividing the parameter by the nominal dose in mg/kg.

TABLE 18

Summary of mean pharmacokinetic parameters for Legs 1-5 of the canine in vivo study of Example 3.

| Parameters | Leg 1 CABOMETYX | Leg 2 ASD-A (HPMC-P; spray dried) | Leg 3 ASD-B (L100-55; spray dried) | Leg 4 ASD-C (PVA-P; spray dried) | Leg 5 ASD-D (HPMC-P; electrosprayed) |
|---|---|---|---|---|---|
| Dose (mg/kg) | 4.78 | 4.75 | 4.76 | 4.78 | 5.05 |
| $C_{max}$ (ng/mL) | 847 | 1342 | 999 | 1409 | 1216 |
| $T_{max}$ (hr) | 1.83 | 1.17 | 2.00 | 1.67 | 1.83 |
| $t_{1/2}$ (hr) | 8.71 | 9.48 | 10.4 | 10.2 | 8.00 |
| $MRT_{last}$ (hr) | 7.96 | 7.36 | 8.86 | 8.34 | 8.72 |
| $AUC_{last}$ (hr · ng/mL) | 5256 | 6570 | 7309 | 8632 | 7694 |
| $AUC_{0\text{-}inf}$ (hr · ng/mL) | 5445 | 6916 | 7792 | 9163 | 8011 |
| | Dose-normalized values[a] | | | | |
| $AUC_{last}$ (hr · kg · ng/mL/mg) | 1112 | 1398 | 1537 | 1809 | 1498 |
| $AUC_{0\text{-}inf}$ (hr · kg · ng/mL/mg) | 1152 | 1469 | 1638 | 1918 | 1559 |

[a]Dose-normalized by dividing the parameter by the nominal dose in mg/kg.

Several observations can be made from the pharmacokinetic data. Independent of formulation, absorption of cabozantinib after peroral administration was rapid. Measurable cabozantinib plasma concentrations were observed at the first time point (30 min post-dose) through the final time point (36 h) for each canine, for each leg of the study. Mean $T_{max}$ values for the five legs ranged between 1.17 hr and 2.00 hr. The terminal phase elimination was well defined for all groups, allowing for calculation of parameters $t_{1/2}$ and $AUC_{0\text{-}inf}$. For the five legs, $t_{1/2}$ values ranged from 8.00 hr to 10.4 hr.

Pharmacokinetic analysis showed that administration of cabozantinib as a CABOMETYX tablet showed little qualitative difference compared to the liquid peroral formulations in legs 2 through 5. However, each ASD formulation (ASD-A through ASD-D) was absorbed to a greater extent than CABOMETYX. In comparing $AUC_{0\text{-}inf}$, each of the ASD formulations showed absorption enhanced by at least 25% as compared to CABOMETYX. This observation indicates that each of the tested ASD formulations may provide enhanced bioavailability if formulated for administration to human subjects or patients.

Finally, a comparison can be made between Leg 2 and Leg 5. The formulation of Leg 2 (ASD-A) included a spray-dried Cabozantinib 50:50 HPMC-P ASD. The formulation of Leg 5 (ASD-D) included an electrosprayed Cabozantinib 50:50 HPMC-P ASD. In a separate experiment, the particle size distribution for the two ASD powders was evaluated, and relevant parameters were determined. The particle size distribution was evaluated using a Horiba LA960 Laser Diffraction Particle Analyzer. The D10/D50/D90 parameters are reported in Table 19.

TABLE 19

Measured parameters of particle size distributions for ASD-A and ASD-D.

| Particle Size Parameter | ASD-A (HPMC-P; spray dried) | ASD-D (HPMC-P; electrosprayed) |
|---|---|---|
| D10 (μ) | 3.78 | 0.18 |
| D50 (μ) | 5.94 | 0.29 |
| D90 (μ) | 9.14 | 0.43 |

Comparing the pharmacokinetic parameters for Leg 2 and Leg 5, $T_{max}$ for ASD-A was somewhat shorter than for ASD-D, but $t_{1/2}$ was somewhat longer. Absolute $C_{max}$ values were within 10%; dose-normalized $C_{max}$ differed by less than 20%. Dose-normalized exposures ($AUC_{last}$ and $AUC_{0\text{-}inf}$) differed by less than 10%. Qualitatively, the pharmacokinetic profiles were largely similar. Accordingly, for the HPMC-P cabozantinib ASDs, it was observed that the difference in characteristic particle sizes for the two ASDs was not a critical parameter for obtaining desirable pharmacokinetic performance.

The foregoing description is given for clearness of understanding only, and no unnecessary limitations should be understood therefrom. Various modifications and alterations to this disclosure will become apparent to those skilled in the art without departing from the scope and spirit of this disclosure. It should be understood that this disclosure is not intended to be unduly limited by the illustrative embodiments and examples set forth herein, and such examples and embodiments are presented by way of example only.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

The term "comprises" and variations such as "comprises" and "comprising" do not have a limiting meaning where these terms appear in the description and claims. Such terms will be understood to imply the inclusion of a stated step or element or group of steps or elements but not the exclusion of any other step or element or group of steps or elements.

By "consists of" (or similarly "consisting of") is meant including, and limited to, whatever follows the phrase "consists of." Thus, the phrase "consists of" in dictates that the listed elements are required or mandatory, and that no other elements may be present. By "consists essentially of" (or similarly "consisting essentially of") is meant including any elements listed after the phrase, and limited to other elements that do not interfere with or contribute to the activity or action specified in the disclosure for the listed elements. Thus, the phrase "consists essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refer to any one of the items in the list and any combination of two or more items in the list.

As used herein, the term "or" is generally employed in its usual sense including "and/or" unless the content clearly dictates otherwise. The term "and/or" means one or all of the listed elements or a combination of any two or more of the listed elements (e.g., preventing and/or treating an affliction means preventing, treating, or both treating and preventing further afflictions).

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50). Also herein, the recitations of numerical ranges by endpoints include all numbers subsumed within that range as well as the endpoints (e.g., 1 to 5 includes 1, 1.5, 2, 2.75, 3, 3.80, 4, 5, etc.) and any sub-ranges (e.g., 1 to 5 includes 1 to 4, 1 to 3, 2 to 4, etc.).

The complete disclosures of the patents, patent documents, and publications cited herein are incorporated by reference in their entirety as if each were individually incorporated. To the extent that there is any conflict or discrepancy between the present disclosure and the disclosure in any document that is incorporated by reference, this disclosure as written will control.

What is claimed is:

1. An amorphous solid dispersion comprising cabozantinib and one or more ionizable polymers;

wherein the cabozantinib and the one or more ionizable polymers are present in a w/w ratio of 20:80 to 80:20 (cabozantinib:polymer).

2. The amorphous solid dispersion of claim 1, wherein the amorphous solid dispersion consists essentially of cabozantinib and the one or more ionizable polymers.

3. The amorphous solid dispersion of claim 1, wherein the one or more ionizable polymers includes at least one polymer that exhibits pH-dependent solubility.

4. The amorphous solid dispersion of claim 1, wherein the one or more ionizable polymers includes an anionic polymer.

5. The amorphous solid dispersion of claim 1, wherein the cabozantinib is cabozantinib free base.

6. The amorphous solid dispersion of claim 1, wherein the cabozantinib is anhydrous cabozantinib free base.

7. The amorphous solid dispersion of claim 1, wherein the cabozantinib is cabozantinib(S)-malate.

8. An amorphous solid dispersion comprising cabozantinib and one or more ionizable polymers;

wherein the cabozantinib and the one or more ionizable polymers are present in a w/w ratio of 20:80 to 80:20 (cabozantinib:polymer); and wherein the one or more ionizable polymers includes an anionic polymer selected from the group consisting of: polyvinyl acetate phthalate, hydroxypropyl methylcellulose acetate succinate, hydroxypropyl methylcellulose phthalate, and methacrylic acid/ethyl acrylate copolymer.

9. The amorphous solid dispersion of claim 8, wherein the amorphous solid dispersion consists essentially of cabozantinib and the anionic polymer.

10. The amorphous solid dispersion of claim 8, wherein the amorphous solid dispersion consists of cabozantinib and the anionic polymer.

11. The amorphous solid dispersion of claim 8, wherein the one or more ionizable polymers includes at least one polymer that exhibits pH-dependent solubility.

12. The amorphous solid dispersion of claim 8, wherein the cabozantinib and the one or more ionizable polymers are present in a w/w ratio of 50:50 (cabozantinib:polymer).

13. The amorphous solid dispersion of claim 8, wherein the cabozantinib is cabozantinib free base.

14. The amorphous solid dispersion of claim 8, wherein the cabozantinib is anhydrous cabozantinib free base.

15. The amorphous solid dispersion of claim 8, wherein the cabozantinib is cabozantinib(S)-malate.

16. An amorphous solid dispersion consisting essentially of cabozantinib and anionic polymer;

wherein the cabozantinib and the anionic polymer are present in a w/w ratio of 20:80 to 80:20 (cabozantinib: polymer); and wherein the anionic polymer is selected from the group consisting of: polyvinyl acetate phthalate, hydroxypropyl methylcellulose acetate succinate, hydroxypropyl methylcellulose phthalate, methacrylic acid/ethyl acrylate copolymer, and combinations thereof.

17. The amorphous solid dispersion of claim 16, wherein the cabozantinib and the anionic polymer are present in a w/w ratio of 50:50 (cabozantinib:polymer).

18. The amorphous solid dispersion of claim 16, wherein the cabozantinib is cabozantinib free base.

19. The amorphous solid dispersion of claim 16, wherein the cabozantinib is anhydrous cabozantinib free base.

20. The amorphous solid dispersion of claim 16, wherein the cabozantinib is cabozantinib(S)-malate.

21. A pharmaceutical composition comprising an amorphous solid dispersion and one or more pharmaceutically acceptable additives;

wherein the amorphous solid dispersion comprises cabozantinib and one or more ionizable polymers;

wherein the cabozantinib and the one or more ionizable polymers are present in a w/w ratio of 20:80 to 80:20 (cabozantinib:polymer).

22. The pharmaceutical composition of claim 21, wherein the one or more ionizable polymers includes at least one polymer that exhibits pH-dependent solubility.

23. The pharmaceutical composition of claim 21, wherein the one or more ionizable polymers includes an anionic polymer.

24. The pharmaceutical composition of claim 21, wherein the one or more ionizable polymers includes an anionic polymer selected from the group consisting of: polyvinyl acetate phthalate, hydroxypropyl methylcellulose acetate succinate, hydroxypropyl methylcellulose phthalate, and methacrylic acid/ethyl acrylate copolymer.

25. The pharmaceutical composition of claim 21, wherein the cabozantinib is cabozantinib free base.

26. The pharmaceutical composition of claim 21, wherein the cabozantinib is anhydrous cabozantinib free base.

27. The pharmaceutical composition of claim 21, wherein the cabozantinib is cabozantinib(S)-malate.

28. The pharmaceutical composition of claim 21, wherein the pharmaceutical composition is a solid dosage form suitable for oral administration.

* * * * *